US008080584B2

(12) United States Patent
Safadi et al.

(10) Patent No.: US 8,080,584 B2
(45) Date of Patent: *Dec. 20, 2011

(54) DELAYED RELEASE RASAGILINE CITRATE FORMULATION

(75) Inventors: Muhammad Safadi, Nazareth (IL); Daniella Licht, Givat Shmuel (IL); Rachel Cohen, Hadera (IL); Anton Frenkel, Netanya (IL); Marina Zholkovsky, Bat-Yam (IL)

(73) Assignee: Teva Pharmaceuticals Industries, Ltd., Petach-Tikva (IL)

(*) Notice: Subject to any disclaimer, the term of this patent is extended or adjusted under 35 U.S.C. 154(b) by 95 days.

This patent is subject to a terminal disclaimer.

(21) Appl. No.: 12/455,976

(22) Filed: Jun. 9, 2009

(65) Prior Publication Data

US 2010/0189787 A1    Jul. 29, 2010

Related U.S. Application Data

(60) Provisional application No. 61/205,833, filed on Jan. 23, 2009.

(51) Int. Cl.
*A01N 33/02* (2006.01)
*A61K 31/135* (2006.01)
(52) U.S. Cl. .................................. 514/647; 614/657
(58) Field of Classification Search .................. 514/647
See application file for complete search history.

(56) References Cited

U.S. PATENT DOCUMENTS

| | | | |
|---|---|---|---|
| 5,387,612 A | 2/1995 | Youdim et al. |
| 5,453,446 A | 9/1995 | Youdim et al. |
| 5,457,133 A | 10/1995 | Youdim et al. |
| 5,486,541 A | 1/1996 | Sterling et al. |
| 5,519,061 A | 5/1996 | Youdim et al. |
| 5,532,415 A | 7/1996 | Youdim et al. |
| 5,576,353 A | 11/1996 | Youdim et al. |
| 5,599,991 A | 2/1997 | Youdim et al. |
| 5,663,415 A | 9/1997 | Chopdekar et al. |
| 5,668,181 A | 9/1997 | Youdim et al. |
| 5,744,500 A | 4/1998 | Youdim et al. |
| 5,786,390 A | 7/1998 | Youdim et al. |
| 5,891,923 A | 4/1999 | Youdim et al. |
| 6,126,968 A | 10/2000 | Peskin et al. |
| 6,277,886 B1 | 8/2001 | Levy et al. |
| 6,316,504 B1 | 11/2001 | Youdim et al. |
| 6,462,222 B1 | 10/2002 | Chorev et al. |
| 6,630,514 B2 | 10/2003 | Youdim et al. |
| 6,956,060 B2 | 10/2005 | Youdim et al. |
| 7,396,860 B2 | 7/2008 | Blaugrund et al. |
| 7,491,847 B2 | 2/2009 | Frenkel |
| 7,547,806 B2 | 6/2009 | Frenkel et al. |
| 7,572,834 B1 | 8/2009 | Sterling et al. |
| 7,598,420 B1 | 10/2009 | Sterling et al. |
| 7,619,117 B1 | 11/2009 | Lidor-Hadas et al. |
| 7,750,051 B2 | 7/2010 | Frenkel et al. |
| 7,815,942 B2 | 10/2010 | Peskin |
| 7,855,233 B2 | 12/2010 | Frenkel et al. |
| 2003/0180332 A1 | 9/2003 | Rimpler et al. |
| 2005/0214372 A1* | 9/2005 | Di Capua et al. .............. 424/472 |
| 2006/0018957 A1 | 1/2006 | Lerner et al. |
| 2006/0094783 A1 | 5/2006 | Youdim et al. |
| 2006/0188581 A1 | 8/2006 | Peskin |
| 2007/0078172 A1 | 4/2007 | McElroy et al. |
| 2007/0093495 A1 | 4/2007 | Ruggero |
| 2007/0100001 A1 | 5/2007 | Youdim et al. |
| 2007/0112217 A1 | 5/2007 | Frenkel |
| 2007/0232700 A1 | 10/2007 | Blaugrund et al. |
| 2008/0161408 A1 | 7/2008 | Frenkel et al. |
| 2008/0199518 A1 | 8/2008 | Ku et al. |
| 2008/0208287 A1 | 8/2008 | Palermo et al. |
| 2008/0261894 A1 | 10/2008 | Kreitman et al. |
| 2009/0062400 A1 | 3/2009 | Oron et al. |
| 2009/0076160 A1 | 3/2009 | Lendvai et al. |
| 2009/0111892 A1 | 4/2009 | Patashnick et al. |
| 2009/0136549 A1 | 5/2009 | Lin et al. |
| 2009/0181086 A1 | 7/2009 | Safadi et al. |
| 2009/0220611 A1 | 9/2009 | Dargelas et al. |
| 2009/0247537 A1 | 10/2009 | Overfield |
| 2009/0312436 A1 | 12/2009 | Levy et al. |
| 2009/0318564 A1 | 12/2009 | Frenkel et al. |
| 2010/0008983 A1 | 1/2010 | Safadi et al. |
| 2010/0010095 A1 | 1/2010 | Frenkel |
| 2010/0010098 A1 | 1/2010 | Elffrink |
| 2010/0029987 A1 | 2/2010 | Allegrini et al. |
| 2010/0137447 A1 | 6/2010 | Lehmann et al. |
| 2010/0144887 A1 | 6/2010 | Frenkel et al. |
| 2010/0145101 A1 | 6/2010 | Frenkel et al. |
| 2010/0168239 A1 | 7/2010 | Poewe |
| 2010/0189788 A1 | 7/2010 | Safadi et al. |
| 2010/0189790 A1 | 7/2010 | Safadi et al. |
| 2010/0189791 A1 | 7/2010 | Safadi et al. |

(Continued)

FOREIGN PATENT DOCUMENTS

WO    WO 95/11016    4/1995

(Continued)

OTHER PUBLICATIONS

U.S. Appl. No. 12/456,642, filed Jun. 19, 2009, Anton Frenkel.
U.S. Appl. No. 12/456,643, filed Jun. 19, 2009, Frenkel et al.
U.S. Appl. No. 12/456,029, filed Jun. 9, 2009, Safadi et al.
U.S. Appl. No. 12/456,031, filed Jun. 9, 2009, Safadi et al.
U.S. Appl. No. 12/456,001, filed Jun. 9, 2009, Safadi et al.
Jul. 8, 2009 Office Action issued in U.S. Appl. No. 12/002,082.
May 2, 2008 International Search Report for PCT International Application No. PCT/US07/025583.
Jun. 16, 2009 International Preliminary Report on Patentability and the Written Opinion of the International Searching Authority for International Appln No. PCT/US07/025583.
U.S. Appl. No. 12/283,022, filed Sep. 8, 2008, Sterling et al.
U.S. Appl. No. 12/283,107, filed Sep. 8, 2008, Sterling et al.
U.S. Appl. No. 12/283,105, filed Sep. 8, 2008, Sterling et al.
U.S. Appl. No. 12/455,969, filed Jun. 10, 2009, Frenkel et al.

(Continued)

*Primary Examiner* — Sreeni Padmanabhan
*Assistant Examiner* — Layla Soroush
(74) *Attorney, Agent, or Firm* — John P. White; Cooper & Dunham LLP

(57) ABSTRACT

Disclosed are formulations which are designed to delay release of rasagiline while maintaining specific pharmacokinetic properties.

41 Claims, No Drawings

U.S. PATENT DOCUMENTS

| | | |
|---|---|---|
| 2010/0190859 A1 | 7/2010 | Frenkel et al. |
| 2010/0234636 A1 | 9/2010 | Stahl |
| 2011/0130466 A1 | 6/2011 | Lorenzl |
| 2011/0152381 A1 | 6/2011 | Frenkel et al. |

FOREIGN PATENT DOCUMENTS

| | | |
|---|---|---|
| WO | WO 98/40102 | 9/1998 |
| WO | WO 2004/089353 | 10/2004 |
| WO | WO 2006/014973 | 2/2006 |
| WO | WO 2006/057912 | 6/2006 |
| WO | WO 2007/102999 | 1/2007 |
| WO | WO 2007/060491 | 5/2007 |
| WO | WO 2008/010768 | 1/2008 |
| WO | WO 2008/019871 | 2/2008 |
| WO | WO 2008/076315 | 6/2008 |
| WO | WO 2008/076348 | 6/2008 |
| WO | WO 2008/131961 | 11/2008 |
| WO | WO 2008/139984 | 11/2008 |
| WO | WO 2009/081148 | 7/2009 |
| WO | WO 2009/122301 | 10/2009 |
| WO | WO 2009/152777 | 12/2009 |
| WO | WO 2010/007181 | 1/2010 |
| WO | WO 2010/013048 | 2/2010 |
| WO | WO 2010/049379 | 5/2010 |
| WO | WO 2010/070090 | 6/2010 |
| WO | WO 2011/003938 | 1/2011 |
| WO | WO 2011/009873 | 1/2011 |
| WO | WO 2011/010324 | 1/2011 |

OTHER PUBLICATIONS

Mar. 16, 2010 International Search Report and the Written Opinion of the International Searching Authority for International Application No. PCT/US10/00174.
Jul. 28, 2000 Amendment filed in the U.S. Appl. No. 09/043,475.
May 2, 2000 Notice of Allowance issued in the U.S. Appl. No. 09/043,475.
Feb. 10, 2000 Amendment filed in the U.S. Appl. No. 09/043,475.
Nov. 10, 1999 Notice of Allowance issued in the U.S. Appl. No. 09/043,475.
Sep. 16, 1999 Amendment filed in the U.S. Appl. No. 09/043,475.
Jun. 16, 1999 Office Action issued in the U.S. Appl. No. 09/043,475.
Jul. 26, 2010 Extended European Search Report issued in European Patent Application No. 10151462.8.
Feb. 12, 2009 Notice of Allowance issued in U.S. Appl. No. 12/002,076.
Jan. 12, 2009 Amendment filed in U.S. Appl. No. 12/002,076.
Jul. 11, 2008 Office Action issued in U.S. Appl. No. 12/002,076.
Azilect®, Physician's Desk Reference (2009), 63th Edition, Thomson Healthcare.
Snodin D., (2006) "Residues of genotoxic alkyl mesylates in mesylate salt drug substances: Real or . . . " Regulatory Toxicology and Pharmacology, vol. 45, pp. 79-90.
"A Controlled Trial of Rasagiline in Early Parkinson . . . ", Archives of Neurology, American Medical Association, Chicago, IL, US, vol. 59, Dec. 1, 2002, pp. 1937-1943.
Gould P L, "Salt Selection for Basic Drugs", International Journal of Pharmaceutics, Elsevier BV, NL Lnkd-DOI:10.1016/0378-5173(86)90055-4, vol. 33, No. 1/03, January.
PCT International Application No. PCT/EP2010/059723, filed Jul. 7, 2010.
Sep. 30, 2010 Extended European Search Report issued in European Patent Application No. 10166534.7.
Feb. 9, 2011 European Search Report issued in European Patent Application No. 10186379.3.
Apr. 12, 2011 Official Action issued in European patent Application No. 10186379.3.
Dec. 8, 2010 Official Acrtion issued in connection with Canadian patent Application No. 2,713,292.
Jan. 7, 2011 Amendment filed in response to Dec. 8, 2010 Official Action issued in connection with Canadian Patent Application No. 2,713,292.
Feb. 22, 2011 Official Action issued in connection with Canadian Patent Application No. 2,713,292.
Mar. 17, 2011 Amendment filed in response to Jan. 7, 2011 Official Action issued in connection with Canadian patent Application No. 2,713,292.
Mar. 23, 2011 Official Action issued in connection with Canadian Patent Application Publication No. 2,727,899.
Jul. 4, 2011 Amendment filed in response to Mar. 23, 2011 Official Action issued in connection with Canadian Patent Application No. 2,727,899.
Jul. 1, 2011 Amendment filed in response to Apr. 12, 2011 Official Action issued in European Patent Application No. 10186379.3.
U.S. Appl. No. 13/140,402, filed Jun. 16, 2011 (Rimkus et al.).

* cited by examiner

DELAYED RELEASE RASAGILINE CITRATE FORMULATION

The application claims benefit of U.S. Provisional Application No. 61/205,833, filed Jan. 23, 2009, the contents of which are hereby incorporated by reference.

Throughout this application various publications, published patent applications, and patents are referenced. The disclosures of these documents in their entireties are hereby incorporated by reference into this application in order to more fully describe the state of the art to which this invention pertains.

BACKGROUND OF THE INVENTION

U.S. Pat. Nos. 5,532,415, 5,387,612, 5,453,446, 5,457,133, 5,599,991, 5,744,500, 5,891,923, 5,668,181, 5,576,353, 5,519,061, 5,786,390, 6,316,504, 6,630,514 disclose R(+)-N-propargyl-1-aminoindan ("R-PAI"), also known as rasagiline. Rasagiline has been reported to be a selective inhibitor of the B-form of the enzyme monoamine oxidase ("MAO-B") and is useful in treating Parkinson's disease and various other conditions by inhibition of MAO-B in the brain.

U.S. Pat. No. 6,126,968 and PCT International Application Publication No. WO 95/11016 disclose pharmaceutical formulations comprising rasagiline. PCT International Application Publication No. WO 2006/014973 also discloses pharmaceutical formulations comprising rasagiline.

AZILECT® is a commercially available rasagiline mesylate immediate release formulation indicated for the treatment of the signs and symptoms of idiopathic Parkinson's disease as initial monotherapy and as adjunct therapy to levodopa. The current marketed formulation of rasagiline (Azilect®) is rapidly absorbed, reaching peak plasma concentration ($t_{max}$) in approximately 1 hour. The absolute bioavailability of rasagiline is about 36%. (AZILECT® Product Label, May 2006).

SUMMARY OF THE INVENTION

The subject application provides a stable oral dosage form comprising a core having rasagiline citrate and at least one pharmaceutically acceptable excipient; and an acid resistant pharmaceutically acceptable coating.

The subject application also provides a method of treating a patient suffering from Parkinson's disease comprising administering to the patient the stable oral dosage form.

DETAILED DESCRIPTION OF THE INVENTION

The subject application provides a stable oral dosage form comprising a core having rasagiline citrate and at least one pharmaceutically acceptable excipient; and an acid resistant pharmaceutically acceptable coating.

In an embodiment of the dosage form, the dosage form when ingested by a human subject provides an AUC value of rasagiline of 80-130% of that of the corresponding amount of rasagiline ingested as an immediate release formulation.

In another embodiment of the dosage form, the dosage form upon administration to a human subject provides an AUC value of rasagiline of 80-125% of that of the corresponding amount of rasagiline ingested as an immediate released formulation.

In yet another embodiment of the dosage form, the dosage form when ingested by a human subject provides a $C_{max}$ of rasagiline 80-145% of that of the corresponding amount of rasagiline ingested as an immediate release formulation.

In yet another embodiment of the dosage form, the dosage form when ingested by a human subject provides a $C_{max}$ of rasagiline of 80-125% of that of the corresponding dosage of rasagiline ingested as an immediate release formulation.

In yet another embodiment of the dosage form, the core further comprises at least one anti-oxidant.

In yet another embodiment of the dosage form, the antioxidant is citric acid.

In yet another embodiment of the dosage form, the core is in the form of a tablet.

In yet another embodiment of the dosage form, the core further comprises at least one disintegrant.

In yet another embodiment of the dosage form, the core comprises between 0.5% and 20% by weight of disintegrant.

In yet another embodiment of the dosage form, the disintegrant is pre-gelatinized starch.

In yet another embodiment of the dosage form, the acid resistant coating layer comprises methacrylic acid-ethyl acrylate copolymer (1:1) and a plasticizer.

In yet another embodiment of the dosage form, in the acid resistant coating layer the ratio of methacrylic acid-ethyl acrylate copolymer (1:1) to plasticizer is between 10 to 1 and 2 to 1.

In yet another embodiment of the dosage form, in the coating the ratio of methacrylic acid-ethyl acrylate copolymer (1:1) to plasticizer is 5 to 1.

In yet another embodiment of the dosage form, the plasticizer is triethyl citrate.

In yet another embodiment of the dosage form, the acid resistant coating layer further comprises talc.

In yet another embodiment of the dosage form, the acid resistant coating is between 3% and 12% by weight of the dosage form.

In yet another embodiment of the dosage form, the acid resistant coating is 8% by weight of the dosage form.

In yet another embodiment of the dosage form, the acid resistant coating comprises two coating layers.

In yet another embodiment of the dosage form, the inner one of the two coating layers comprises hypromellose.

In yet another embodiment of the dosage form, the dosage form is less than 150 mg by weight.

In yet another embodiment of the dosage form, the content of rasagiline citrate in the dosage form is 0.74 mg to 3.63 mg.

In yet another embodiment of the dosage form, the content of rasagiline citrate in the dosage form is 0.74 mg to 1.82 mg.

In yet another embodiment of the dosage form, the content of rasagiline citrate in the dosage form is 1.58 mg to 3.63 mg.

In yet another embodiment of the dosage form, the content of rasagiline in the dosage form is 0.5 mg.

In yet another embodiment of the dosage form, the content of rasagiline in the dosage form is 1.0 mg.

In yet another embodiment of the dosage form, the dosage form in addition to the rasagiline citrate comprises mannitol, colloidal silicon dioxide, starch NF, pregelatinized starch, stearic acid, talc, hypromellose, methacrylic acid ethyl acrylate copolymer, talc extra fine, and triethyl citrate.

In yet another embodiment of the dosage form, the dosage form comprises 79.84 mg of mannitol, 0.6 mg of colloidal silicon dioxide, 10.0 mg of starch NF, 20.0 mg of pregelatinized starch, 2.0 mg of stearic acid, 2.0 mg of talc, 4.8 mg of hypromellose, 6.25 mg of methacrylic acid-ethyl acrylate copolymer, 1.25 mg of triethyl citrate, and 3.1 mg of talc extra fine.

In yet another embodiment of the dosage form, the dosage form comprises 67.8 mg of mannitol, 0.6 mg of aerosil, 10.0 mg of starch NF, 20.0 mg of pregelatinized starch, 2.0 mg of stearic acid, 2.0 mg of talc, 4.8 mg of hypromellose, 4.0 mg of methacrylic acid ethyl acrylate copolymer, 0.8 mg of triethyl citrate, and 1.9 mg of talc extra fine.

In yet another embodiment of the dosage form, the dosage form comprises 80.34 mg of mannitol, 0.6 mg of aerosil, 10.0 mg of starch NF, 20.0 mg of pregelatinized starch, 2.0 mg of stearic acid, 2.0 mg of talc, 4.8 mg of hypromellose, 6.25 mg of methacrylic acid ethyl acrylate copolymer, 1.25 mg of triethyl citrate, and 3.1 mg of talc extra fine.

In yet another embodiment of the dosage form, the dosage form comprises 68.3 mg of mannitol, 0.6 mg of aerosil, 10.0 mg of starch NF, 20.0 mg of pregelatinized starch, 2.0 mg of stearic acid, 2.0 mg of talc, 4.8 mg of hypromellose, 4.0 mg of methacrylic acid ethyl acrylate copolymer, 0.8 mg of triethyl citrate, and 1.9 mg of talc extra fine.

In yet another embodiment of the dosage form, the dosage form releases between 80 and 100% of rasagiline when placed in a basket apparatus in 500 mL of buffered aqueous media at a pH of 6.8 at 37° C. at 75 revolutions per minute for 20 minutes.

In yet another embodiment of the dosage form, the dosage form further comprises rasagiline base.

In yet another embodiment of the dosage form, up to 2% of the total amount of rasagiline in the dosage form is present as rasagiline free base.

In yet another embodiment of the dosage form, the total amount of non-polar impurities in the dosage form is less than 0.3 wt % relative to the amount of rasagiline.

In yet another embodiment of the dosage form, the amount of N-(2-Chloroallyl)-1(R)-aminoindan content in the dosage form is less than 20 ppm relative to the amount of rasagiline.

In yet another embodiment of the dosage form, the amount of N-(2-Chloroallyl)-1(R)-aminoindan content in the dosage form is less than 4 ppm relative to the amount of rasagiline.

In yet another embodiment of the dosage form, the dosage form when ingested by a human subject achieves MAO-B inhibition substantially the same as that of the corresponding dosage of rasagiline ingested as an immediate release formulation.

The subject application also provides a method of treating a patient suffering from Parkinson's disease comprising administering to the patient the dosage form of any one of claims 1-34.

In an embodiment of the method, the patient suffers from delayed gastric emptying.

By any range disclosed herein, it is meant that all hundredth, tenth and integer unit amounts within the range are specifically disclosed as part of the invention. Thus, for example, 0.01 mg to 50 mg means that 0.02, 0.03 . . . 0.09; 0.1, 0.2 . . . 0.9; and 1, 2 . . . 49 mg unit amounts are included as embodiments of this invention.

Citric acid is a weak organic acid, and is triprotic. Therefore, the rasagiline citrate described herein may exist in mono-, di- or tri-rasagiline citrate form or a mixture thereof.

An immediate release formulation of rasagiline is AZILECT® Tablets which contain rasagiline (as the mesylate), a propargylamine-based drug indicated for the treatment of idiopathic Parkinson's disease. It is designated chemically as: 1H-Inden-1-amine, 2,3-dihydro-N-2-propynyl-, (1R)-, methanesulfonate.

MAO inhibitors that selectively inhibit MAO-B are largely devoid of the potential to cause the "cheese effect". Nonetheless, the possibility exists that delayed gastric emptying of R-PAI may contribute to this phenomenon. Therefore, a goal in developing the formulations of the current invention was to develop a delayed release, enteric coated formulation comprising rasagiline in an amount equivalent to 1 mg of rasagiline base which would release the active ingredient in the duodenum and/or the jejunum, past the stomach.

During the development of the formulations of the current invention, it was determined that the formulations should meet the criteria of bioequivalence to the known, immediate release rasagiline mesylate formulations (as disclosed in example 1, for example) in a single dose bio-equivalence study in healthy subjects. These criteria include similarity of $C_{max}$ and $AUC_{0-t}$ (area under the curve) within the range of 80-125% within a 90% confidence interval between the new formulations and the known, immediate release formulations. The difference between the two formulations should be evident in bioequivalence studies as a difference in $t_{max}$. In other words, the mean pharmacokinetic profile of the formulations of the current invention should substantially match the mean pharmacokinetic profile of the formulations of the known immediate release formulation, with the exception of the $t_{max}$ which should be greater for the delayed release formulation than for the immediate release formulation.

The reason for attempting to match the mean $C_{max}$ and $AUC_{0-t}$ of the known immediate release formulation (i.e. to formulate a delayed release formulation that is bioequivalent) is that the efficacy of the immediate release formulation has been proven, and it is likely that the efficacy of the formulation relates to its mean $C_{max}$ and/or AUC. (Arch Neurol. 2002; 59:1937-1943.)

In order to reach this target, development was directed toward enteric coated tablets having a quickly disintegrating core with an enteric coating which allows release of the rasagiline in a very specific range of pH. This specific pH range would prevent the formulation from releasing rasagiline in the stomach, and would allow the formulation to release rasagiline quickly under the physiological conditions of the intestine.

In PCT International Application Publication No. WO 2006/014973, delayed release rasagiline mesylate pharmaceutical formulations were disclosed. In the disclosed formulations (Example 1, 2 and 4) methacrylic acid-ethyl acrylate copolymer (1:1) 30% dispersion, known as Eudragit® L-30 D-55 was used. As evident from WO 2006/014973, these formulations were indeed delayed-release formulations as shown by their dissolution profiles and by the in-vivo data, however, their pharmacokinetic profile, in terms of mean $C_{max}$ did not match the pharmacokinetic profile of the immediate release rasagiline mesylate formulations.

The excipient methacrylic acid-ethyl acrylate copolymer (1:1) 30% dispersion, known as Eudragit® L-30 D-55, used in the above-mentioned publication WO 2006/014973, when applied as an aqueous dispersion either on tablets or on spheres prevents dissolution of the coated composition at low acidic pH. The structure of this polymer is as follows:

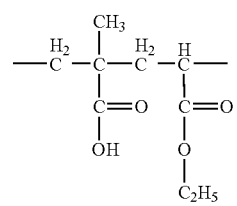

The ratio of the free carboxyl groups to the ester groups is approximately 1:1. The average molecular weight is approximately 250,000.

When this excipient is used in an aqueous dispersion or in an organic solution and formed into a film coating of a pharmaceutical formulation, it is intended to dissolve at a pH of about 5.5. (Aqueous Polymeric Coatings for Pharmaceutical Dosage Forms; Second Edition, Revised and Expanded. Ed. James W. McGinity, 1997.) Without wishing to be bound by any theory, it is possible that these prior art formulations began to dissolve in lower pH in the stomach, perhaps in the presence of food which can raise the pH in the stomach, and continued to dissolve over a prolonged period of time in the duodenum and the jejunum. It may also start releasing after the stomach. The prolonged dissolution period could explain why the $C_{max}$ of these prior art formulations was significantly lower than the $C_{max}$ of the immediate release formulations to which they were compared.

In general, the release process encompasses three major steps:

1. Transport to the site where the pH is high enough to initiate release from the dosage form;
2. Dissolution of the coating; and
3. Disintegration and release of the drug from the core.

For highly soluble compounds the third step is the most crucial. In contrast, for enteric coated pellets for which emptying occurs gradually, not all at once, the first step has a major influence on the PK profile. As pellets empty at different times, they reach the second step at different time points as well. Therefore the PK profile is a superimposition of multiple "mini" PK profiles.

The delayed release compositions of the current invention are intended to withstand pH conditions of 6.0 and are intended to release the active ingredient only above that pH. This specific pH was chosen in order to attempt to minimize any possible dissolution of the pharmaceutical compositions of the invention in the stomach in fed condition and to allow rapid dissolution of the pharmaceutical compositions of the invention after the stomach in the duodenum and/or the jejunum. The ability of a pharmaceutical formulation to enter the duodenum before releasing rasagiline and subsequently releasing the rasagiline rapidly after the stomach provides a pharmacokinetic profile, and specifically a $C_{max}$ and $AUC_{0-t}$, similar to that of the known immediate release formulation.

Achieving the goal of a delayed-release pharmaceutical formulation in which the $C_{max}$ is similar to the corresponding immediate-release formulation is not trivial to achieve. In general, when delayed release formulations are compared to their immediate release counterparts in bio-studies, the $C_{max}$ of the delayed release formulations are lower than the $C_{max}$ in the corresponding immediate release formulations. (Mascher, et al. Arneimittelforschung. 2001; 51(6): 465-9. Behr, et al. J. Clin Pharmacol. 2002; 42(7): 791-7.)

In addition, the instant invention provides a solution to the problem of peripheral MAO inhibition by providing pharmaceutical dosage forms comprising rasagiline which are adapted to inhibit the release or absorption of rasagiline in the stomach (i.e. delay the release of rasagiline until at least a portion of the dosage form has traversed the stomach). This avoids or minimizes absorption of rasagiline in the stomach, thereby avoiding or minimizing the potential cheese effect.

The pharmaceutical dosage form may be comprised of an acid resistant excipient which prevents the dosage form or parts thereof from contacting the acidic environment of the stomach. The acid resistant excipient may coat the rasagiline in the form of an enteric coated tablet, capsule, hard or soft gelatin capsule. Enteric coating, in the context of this invention, is a coating which prevents the dissolution of an active ingredient in the stomach. This is determined by measuring the dissolution of the pharmaceutical dosage form in acidic solution, as defined by USP methods. Even in enteric pharmaceutical dosage forms, some of the dosage form may dissolve in the stomach; however, the dosage form may still be considered enteric according to USP standards.

In all of its aspects, the present invention provides an oral pharmaceutical dosage form useful for treating: Parkinson's disease, brain ischemia, head trauma injury, spinal trauma injury, neurotrauma, neurodegenerative disease, neurotoxic injury, nerve damage, dementia, Alzheimer's type dementia, senile dementia, depression, memory disorders, hyperactive syndrome, attention deficit disorder, multiple sclerosis, schizophrenia, and/or affective illness, but with a reduced risk of peripheral MAO inhibition that is typically associated with administration of rasagiline with known oral dosage forms.

Specific examples of pharmaceutically acceptable carriers and excipients that may be used to formulate oral dosage forms of the present invention are described, e.g., in U.S. Pat. No. 6,126,968 to Peskin et al., issued Oct. 3, 2000. Techniques and compositions for making dosage forms useful in the present invention are described, for example, in the following references: 7 Modern Pharmaceutics, Chapters 9 and 10 (Banker & Rhodes, Editors, 1979); Pharmaceutical Dosage Forms: Tablets (Lieberman et al., 1981); Ansel, Introduction to Pharmaceutical Dosage Forms 2nd Edition (1976); Remington's Pharmaceutical Sciences, 17th ed. (Mack Publishing Company, Easton, Pa., 1985); Advances in Pharmaceutical Sciences (David Ganderton, Trevor Jones, Eds., 1992); Advances in Pharmaceutical Sciences Vol 7. (David Ganderton, Trevor Jones, James McGinity, Eds., 1995); Aqueous Polymeric Coatings for Pharmaceutical Dosage Forms (Drugs and the Pharmaceutical Sciences, Series 36 (James McGinity, Ed., 1989); Pharmaceutical Particulate Carriers: Therapeutic Applications: Drugs and the Pharmaceutical Sciences, Vol 61 (Alain Rolland, Ed., 1993); Drug Delivery to the Gastrointestinal Tract (Ellis Horwood Books in the Biological Sciences. Series in Pharmaceutical Technology; J. G. Hardy, S. S. Davis, Clive G. Wilson, Eds.); Modern Pharmaceutics Drugs and the Pharmaceutical Sciences, Vol 40 (Gilbert S. Banker, Christopher T. Rhodes, Eds.).

Tablets may contain suitable binders, lubricants, disintegrating agents, coloring agents, flavoring agents, flow-inducing agents, melting agents, stabilizing agents, solubilizing agents, antioxidants, buffering agent, chelating agents, fillers and plasticizers. For instance, for oral administration in the dosage unit form of a tablet or capsule, the active drug component can be combined with an oral, non-toxic, pharmaceutically acceptable, inert carrier such as gelatin, agar, starch, methyl cellulose, dicalcium phosphate, calcium sulfate, mannitol, sorbitol, microcrystalline cellulose and the like. Suitable binders include starch, gelatin, natural sugars such as corn starch, natural and synthetic gums such as acacia, tragacanth, or sodium alginate, povidone, carboxymethylcellulose, polyethylene glycol, waxes, and the like. Antioxidants include ascorbic acid, fumaric acid, citric acid, malic acid, gallic acid and its salts and esters, butylated hydroxyanisole, editic acid. Lubricants used in these dosage forms include sodium oleate, sodium stearate, sodium benzoate, sodium acetate, stearic acid, sodium stearyl fumarate, talc and the like. Disintegrators include, without limitation, starch, methyl cellulose, agar, bentonite, xanthan gum, croscarmellose sodium, sodium starch glycolate and the like, suitable plasticizers include triacetin, triethyl citrate, dibutyl sebacate, polyethylene glycol and the like.

The basket-type apparatus used in this invention is the apparatus 1 described in the United States Pharmacopeia, $29^{th}$ Edition (2006), chapter 711. The apparatus is constructed as follows:

The assembly consists of the following: a covered vessel made of glass or other inert, transparent material; a motor; a metallic drive shaft; and a cylindrical basket. The vessel is partially immersed in a suitable water bath of any convenient size or placed in a heating jacket. The water bath or heating jacket permits holding the temperature inside the vessel at 37±0.5 during the test and keeping the bath fluid in constant, smooth motion. No part of the assembly, including the environment in which the assembly is placed, contributes significant motion, agitation, or vibration beyond that due to the smoothly rotating stirring element. Apparatus that permits observation of the specimen and stirring element during the test is preferable. The vessel is cylindrical, with a hemispherical bottom and with one of the following dimensions and capacities: for a nominal capacity of 1 L, the height is 160 mm to 210 mm and its inside diameter is 98 mm to 106 mm; for a nominal capacity of 2 L, the height is 280 mm to 300 mm and its inside diameter is 98 mm to 106 mm; and for a nominal capacity of 4 L, the height is 280 mm to 300 mm and its inside diameter is 145 mm to 155 mm. Its sides are flanged at the top. A fitted cover may be used to retard evaporation. The shaft is positioned so that its axis is not more than 2 mm at any point from the vertical axis of the vessel and rotates smoothly and without significant wobble. A speed-regulating device is used that allows the shaft rotation speed to be selected and maintained at the rate specified in the individual monograph, within ±4%. Shaft and basket components of the stirring element are fabricated of stainless steel type 316 or equivalent.

Unless otherwise specified in the individual monograph, use 40-mesh cloth. A basket having a gold coating 0.0001 inch (2.5 μm) thick may be used. The dosage unit is placed in a dry basket at the beginning of each test. The distance between the inside bottom of the vessel and the basket is maintained at 25±2 mm during the test.

Due to the sensitivity of rasagiline base to UV radiation and light in general, during the preparation of formulations described in the following examples, it is recommended to perform the process in a low UV radiation environment, preferably in an environment without any UV radiation.

This invention will be better understood from the experimental details which follow. However, one skilled in the art will readily appreciate that the specific methods and results discussed are merely illustrative of the invention as described more fully in the claims which follow thereafter.

Example 1

Rasagiline Immediate Release Tablets

Rasagiline immediate release tablets were prepared using the ingredients listed in Table 1.

TABLE 1

| Component | Function | Per Tablet (mg) (0.5 mg Rasagiline base) | Per Tablet (mg) (1 mg Rasagiline base) |
|---|---|---|---|
| Rasagiline mesylate | | 0.78 | 1.56 |
| Mannitol | Filler | 79.62 | 159.24 |
| Aerosil | Flowing Agent | 0.6 | 1.2 |
| Starch NF | Binder | 10.0 | 20.0 |
| Starch, Pregelatinized (Starch STA-RX 1500) | Disintegrant | 10.0 | 20.0 |
| Talc | Lubricant | 2.0 | 4.0 |
| Stearic Acid | Lubricant | 2.0 | 4.0 |
| Total core Tablet Weight | | 105 | 210 |

Rasagiline mesylate, mannitol, half of the colloidal silicon dioxide, starch and pregelatinized starch were mixed in a Diosna P-800 mixer for about 5 minutes. Water was added and the mixture was mixed further. The granulate was dried and the remainder of the colloidal silicon dioxide was added. The granulate was ground in a Frewitt mill and stearic acid and talc were added. The granulate was mixed for five minutes in a tumbler and was tableted.

Example 2

Rasagiline Base Tablet Cores

An attempt was made to formulate tablet cores which would have a pharmacokinetic profile ($C_{max}$ and AUC) resembling that of the immediate release formulation of example 1.

A process for preparing crystalline rasagiline base is disclosed in U.S. Patent Application Publication No. 2008/0161408 (and which corresponds substantially to WO 2008/076348). In particular, the document describes a process for manufacture of crystalline rasagiline base which comprises: a) dissolving a salt of R(+)-N-propargyl-1-aminoindan in water to form a solution; b) cooling the solution to a temperature of about 0-15° C.; c) basifying the solution to a pH of about 11 to form a suspension; and d) obtaining the crystalline rasagiline base from the suspension.

Five preliminary formulations of rasagiline base as API were prepared using standard tableting technique based on rasagiline immediate release formulation of example 1. Different reagents were added in order to stabilize the API within the formulation.

TABLE 2

| Compositions of rasagiline base tablet cores: | | | | |
|---|---|---|---|---|
| Composition 1 | Composition 2 | Composition 3 | Composition 4 | Composition 5 |
| Rasagiline base | Rasagiline base | Rasagiline base | Rasagiline base | Rasagiline base |
| Citric Acid | Maleic Acid | Succinic Acid | Malic Acid | BHT |
| Mannitol USP/EP | Mannitol USP/EP | Mannitol USP/EP | Mannitol USP/EP | Mannitol USP/EP |
| Colloidal Silicon Dioxide | Colloidal Silicon Dioxide | Colloidal Silicon Dioxide | Colloidal Silicon Dioxide | Colloidal Silicon Dioxide |
| Pregelatinized Starch | Pregelatinized Starch | Pregelatinized Starch | Pregelatinized Starch | Pregelatinized Starch |
| Starch NF/EP | Starch NF/EP | Starch NF/EP | Starch NF/EP | Starch NF/EP |

TABLE 2-continued

Compositions of rasagiline base tablet cores:

| Composition 1 | Composition 2 | Composition 3 | Composition 4 | Composition 5 |
|---|---|---|---|---|
| Stearic Acid | Stearic Acid | Stearic Acid | Stearic Acid | Stearic Acid |
| Talc | Talc | Talc | Talc | Talc |

The batches were produced in lab scale of ~500 tablets using laboratory equipment with non-GMP lot of API.

Stability results of all five formulations (final mixtures) were put on short-term stability studies at accelerated and room temperature conditions. Stability results, content of each formulation and dissolution results of tablets compressed using single punch are presented in the tables below.

Composition 1

| Mg/tab | Raw Materials | | Time 0 | 2 wks 25° C. | 2 wks 40° C. | 1 mo 40° C. |
|---|---|---|---|---|---|---|
| 0.82 | Citric Acid | | Assay stability results (%) | | | |
| | Water | | 101.6% | 94.2% | 94.8% | 98.0% |
| 1.00 | Rasagiline base | | | | | |
| 80.0 | Manitol USP/EP | | | | | |
| 0.3 | Aerosil 200 | | | | | |
| 10.0 | Starch NF/EP | | Stability Results - Level of Impurity (%) | | | |
| 20.0 | Starch STA-RX 1500 | Total Impurity | <0.04 (DL) | <0.04 (DL) | <0.1 (QL) | <0.2 (QL) |
| 0.3 | Aerosil 200 | | | | | |
| 2.0 | Stearic Acid | | | | | |
| 2.0 | Talc | | | | | |
| 116.42 | Total weight | | | | | |

Composition 2

| Mg/tab | Raw Materials | | Time 0 | 2 wks 25° C. | 2 wks 40° C. | 1 mo 40° C. |
|---|---|---|---|---|---|---|
| 0.7 | Maleic Acid | | Assay stability results (%) | | | |
| | Water | | 82.3 | 84.6 | 79.8 | 80.8 |
| 1.00 | Rasagiline base | | | | | |
| 80.0 | Manitol USP/EP | | | | | |
| 0.3 | Aerosil 200 | | Stability Results - Level of Impurity (%) | | | |
| 10.0 | Starch NF/EP | Total Impurity | <0.1 (QL) | 0.1 | 0.4 | 0.8 |
| 20.0 | Starch STA-RX 1500 | | | | | |
| 0.3 | Aerosil 200 | | | | | |
| 2.0 | Stearic Acid | | | | | |
| 2.0 | Talc | | | | | |
| 116.3 | Total weight | | | | | |

Composition 3

| Mg/tab | Raw Materials | | Time 0 | 2 wks 25° C. | 2 wks 40° C. | 1 mo 40° C. |
|---|---|---|---|---|---|---|
| 0.7 | Succinic Acid | | Assay stability results (%) | | | |
| | Water | | 102.9 | 99.4 | 100.6 | 101.9 |
| 1.00 | Rasagiline base | | | | | |
| 80.0 | Manitol USP/EP | | Stability Results - Level of Impurity (%) | | | |
| 0.3 | Aerosil 200 | Total Impurity | 0.4 | 0.4 | 0.6 | 1.2 |
| 10.0 | Starch NF/EP | | | | | |
| 20.0 | Starch STA-RX 1500 | | | | | |
| 0.3 | Aerosil 200 | | | | | |
| 2.0 | Stearic Acid | | | | | |
| 2.0 | Talc | | | | | |
| 116.3 | Total weight | | | | | |

Composition 4

| Mg/tab | Raw Materials | | Time 0 | 2 wks 25° C. | 2 wks 40° C. | 1 mo 40° C. |
|---|---|---|---|---|---|---|
| 0.8 | Malic Acid | | Assay stability results (%) | | | |
| | Water | | 103.4 | 101.5 | 101.5 | 102.2 |
| 1.00 | Rasagiline base | | | | | |
| 80.0 | Manitol USP/EP | | | | | |
| 0.3 | Aerosil 200 | | | | | |
| 10.0 | Starch NF/EP | | Stability Results - Level of Impurity (%) | | | |
| 20.0 | Starch STA-RX 1500 | Total Impurity | <0.04 (DL) | <0.04 (DL) | <0.1 (QL) | <0.2 (QL) |
| 0.3 | Aerosil 200 | | | | | |
| 2.0 | Stearic Acid | | | | | |
| 2.0 | Talc | | | | | |
| 116.4 | Total weight | | | | | |

Composition 5

| Mg/tab | Raw Materials | | Time 0 | 2 wks 25° C. | 2 wks 40° C. | 1 mo 40° C. |
|---|---|---|---|---|---|---|
| | Ethanol 95% | | Assay stability results (%) | | | |
| 0.02 | BHT | | 67.8 | 65.7 | 48.5 | 31.9 |
| 1.00 | Rasagiline base | | | | | |
| 80.0 | Manitol USP/EP | | Stability Results - Level of Impurity (%) | | | |
| 0.3 | Aerosil 200 | Total Impurity | <0.1 (QL) | <0.1 (QL) | 2.9 | 5.7 |
| 10.0 | Starch NF/EP | | | | | |
| 20.0 | Starch STA-RX 1500 | | | | | |
| 0.3 | Aerosil 200 | | | | | |
| 2.0 | Stearic Acid | | | | | |
| 2.0 | Talc | | | | | |
| 115.62 | Total weight | | | | | |

Dissolution Results (% in 0.1N HCl)

| | 5 min | 10 min | 15 min |
|---|---|---|---|
| Composition 1 | 85 | 99 | 100 |
| Composition 2 | 49 | 82 | 90 |
| Composition 3 | 62 | 98 | 103 |
| Composition 4 | 59 | 100 | 107 |
| Composition 5 | 70 | 70 | 70 |

Dissolution Results (% in Phosphate buffer pH 6.8)

| | 5 min | 10 min | 15 min |
|---|---|---|---|
| Composition 1 | 78 | 92 | 94 |
| Composition 2 | 40 | 77 | 82 |
| Composition 3 | 59 | 98 | 101 |
| Composition 4 | 59 | 95 | 102 |
| Composition 5 | 70 | 70 | 70 |

Discussion:

Compositions 1 and 4, which contain antioxidants Citric and Malic acids respectively, gave the best stability results and satisfactory dissolution profile. Therefore, they were chosen for future development.

Example 3a

Preparation of Rasagiline Base Delayed Release Enteric Coated Tablet—Formulation I In this example, a 1 mg rasagiline base delayed release enteric coated tablet containing citric acid (117 mg core tablet weight) was prepared.

TABLE 3a

Composition of rasagiline base delayed release enteric coated tablet

| Component | Function | Per Tablet (mg) |
|---|---|---|
| Core tablets | | |
| Rasagiline Base | Drug Substance | 1.0 |
| Citric Acid | Antioxidant/Stabilizer | 1.6 |
| Mannitol | Filler | 79.84 |
| Colloidal Silicon Dioxide | Flowing Agent | 0.6 |
| Starch NF | Binder | 10.0 |
| Starch, Pregelatinized (STA-RX ® 1500) | Disintegrant | 20.0 |
| Talc | Lubricant | 2.0 |
| Stearic Acid | Lubricant | 2.0 |
| Total Core Tablet Weight | | 117.0 |
| Subcoating | | |
| Pharmacoat ® 606 (Hypromellose USP) Granules | Coating Agent | 4.8 |
| Purified Water Coating Suspension | Processing Agent | |
| Eudragit ® L-30D-55 | Coating Agent | 6.250* |
| Talc USP Extra Fine | Lubricant | 1.25 |
| Triethyl citrate | Plasticizer | 3.1 |
| Purified Water | Processing Agent | |
| Total Tablet Weight | | 132.4 |

*Dry substance remaining on the core.

I. Dry Mixing:

Mannitol, half amount of Aerosil, Pregelatinized Starch and Starch NF were placed in a high shear granulating mixer and were premixed for 1 minute mixing at mixer speed I, followed by 1 minute mixing at mixer speed I, and chopper I.

II. Wet Granulation:

Citric acid solution was prepared using 320 g of citric acid, in purified water in a weight ratio of approximately 1:10.6 to 1:6.

Rasagiline Base was added with stirring for approximately 15 minutes. The stirring was continued until a clear solution was observed. The solution was added into a high shear granulating mixer and the content was mixed for approximately 2 minutes at mixer speed II and chopper II. An extra amount of water was added into the high shear granulating mixer, and the solution was mixed for two more minutes at mixer speed II and chopper II.

The wet granulate was discharged into a fluid bed dryer trolley at mixer speed I.

III. Fluid Bed Drying:

The material from step II was dried in a fluid bed dryer under inlet air temperature of 45° C. (40° to 50° C.) and outlet air temperature of maximum 37-38° C.

IV. Milling:

The dry granulate and the residual amount of Aerosil were milled through an oscillating granulator with screen 0.6 mm into a storage container.

The milled granulate was further weighted.

V. Final Blending:

Stearic Acid and Talc were sieved through a 50 mesh screen and were transferred to the Y-cone/Bin.
1. The mixture was mixed for 5 minutes.
2. The Final Blend and the percentage yield were determined.

3. The final blend was stored in a container using an inner transparent polyethylene bag and an outer black polyethylene bag. Two Silica gel pillows were placed between the two polyethylene bags.
4. Samples were taken for a Blend Uniformity test.

VI. Tablet Compression:

A tablet compression machine (FETTE 1200) was set up with the designated punches 6.0 mm.

The in-process control testing for tablets included average weight, individual weight, thickness, hardness, friability and disintegration.

In process control specifications for Rasagiline Base DR 1 mg tablets is:

| Parameter | Minimum | Target | Maximum |
|---|---|---|---|
| Average weight (mg) | 111 | 117 | 123 |
| Individual weight (mg) | 111 | 117 | 123 |
| Thickness (mm) | 3.3 | 3.6 | 3.9 |
| Hardness (SCU) | 7 | 9 | 11 |
| Friability (%) | — | — | 1.0 |
| Disintegration (minutes) | — | — | 5 |

The tablets were weighted and the percentage yield was calculated.

VII. Sub-Coating:

Tablet cores were first coated with hypromellose (Pharmacoat 606®) as a pre-coating, followed by coating with Methacrylic Acid-Methyl Methacrylate Copolymer [1:1] (30% dispersion of Eudragit® L100-55) to prevent any possible interaction between the Rasagiline base in the core and the Eudragit L polymer.

1. Preparation of Pharmacoat 606® solution:
   Hypromellose USP solution was prepared using hypromellose, in purified water in a weight ratio of approximately 1:10.
2. Pre heating:
   The tablet cores were placed in an (Ohara) Coater coating pan. The tablets were heated under inlet air temperature of 50° C. (45° to 55° C.) and outlet air temperature of 45-50° C.
3. Spraying process:
   The tablet cores were sprayed with hypromellose solution in the Ohara Coater coating pan. The inlet air temperature was 50° C.; the outlet, air temperature was 35° C. The pan speed was set to 16 rpm (can vary from 14 to 18 rpm). Spraying rate was 15-35 gr/min. The tablets were dried for 1 hour with inlet air temperature of 45° C. (temperature range is 40° C.-50° C.).

VIII. Enteric Coating:

1. Preparation of Enteric Coating dispersion of Eudragit® L100-55:
   Triethyl citrate was mixed with water for 15 minutes. The Talc Extra fine was added into the Triethyl citrate and water dispersion in an Ultraturax within 10 minutes. Eudragit L100-55 30% dispersion was added to Triethyl citrate/talc dispersion, filtered and stirred.
2. Pre heating:
   The precoated tablets were placed in an Ohara Coater coating pan. The tablets were heated under inlet air temperature of 50° C. (45° to 55° C.) and outlet air temperature of 45° C. (40° to 50° C.)
3. Spraying process:
   The tablets were sprayed with the dispersion in an Ohara coater pan. The inlet air temperature was in the range of 40° C.-50 the outlet air temperature was in the range of 30-40° C. The pan speed was set to 16 rpm in range of 14-18 rpm, and the spraying rate was 5-20 gr/min. The tablets were dried for 2 hours. The inlet air temperature was 50° C. on minimum pan speed.

EUDRAGIT® L 100-55 contains an anionic copolymer based on methacrylic acid and ethyl acrylate. It is also known as methacrylic acid copolymer, type C. The ratio of the free carboxyl groups to the ester groups is approx. 1:1. The average molecular weight is approx. 250,000.

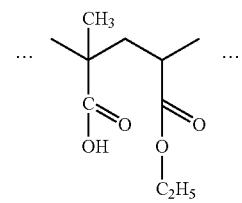

Example 3b

Preparation of 1 mg Rasagiline Base Delayed Release Enteric Coated Tablet—Formulation III In this example, a 1 mg rasagiline base delayed release enteric coated tablet containing citric acid (76 mg core tablet weight) was prepared using similar steps as described in example 3a.

TABLE 3b composition of rasagiline-base delayed release enteric coated tablet

| Component | Function | Per Tablet (mg) |
|---|---|---|
| Core tablets | | |
| Rasagiline base | Drug Substance | 1.0 |
| Citric acid | Antioxidant/Stabilizer | 1.6 |
| Mannitol | Filler | 45.0 |
| Aerosil | Flowing Agent | 0.4 |
| Starch NF | Binder | 5.0 |
| Starch, Pregelatinized (Starch STA-RX 1500) | Disintegrant | 20.0 |
| Talc | Lubricant | 1.5 |
| Stearic Acid | Lubricant | 1.5 |
| Total Core Tablet Weight | | 76.0 |
| Subcoating | | |
| Pharmacoat ® 606 (Hypromellose USP) Granules | Coating Agent | 3.5 |
| Purified Water Coating Suspension | Processing Agent | |
| Eudragit ® L-30D-55 | Coating Agent | 4.0* |
| Talc USP Extra Fine | Lubricant | 1.9 |
| Triethyl citrate NF | Plasticizer | 0.8 |
| Purified Water | Processing Agent | |
| Total Tablet weight | | 86.2 |

*Dry substance remaining on the core.

Example 3c

Preparation of 0.5 mg Rasagiline Base Delayed Release Enteric Coated Tablet

In this example, a 0.5 mg rasagiline base delayed release enteric coated tablet containing citric acid (117 mg core tablet weight) was prepared using similar steps as described in example 3a.

TABLE 3c composition of rasagiline-base delayed release enteric coated tablet

| Component | Function | Per Tablet (mg) |
|---|---|---|
| Core tablets | | |
| Rasagiline base | Drug Substance | 0.5 |
| Citric acid | Antioxidant/Stabilizer | 1.6 |
| Mannitol | Filler | 80.34 |
| Aerosil | Flowing Agent | 0.6 |
| Starch NF | Binder | 10.0 |
| Starch, Pregelatinized (Starch STA-RX 1500) | Disintegrant | 20.0 |
| Talc | Lubricant | 2.0 |
| Stearic Acid | Lubricant | 2.0 |
| Total Core Tablet Weight | | 117.0 |
| Subcoating | | |
| Pharmacoat ® 606 (Hypromellose USP) Granules | Coating Agent | 4.8 |
| Purified Water Coating Suspension | Processing Agent | |
| Eudragit ® L-30D-55 | Coating Agent | 6.25* |
| Talc USP Extra Fine | Lubricant | 3.1 |
| Triethyl citrate NF | Plasticizer | 1.25 |
| Purified Water | Processing Agent | |
| Total Tablet weight | | 132.4 |

*Dry substance remaining on the core.

Example 3d

Preparation of 0.5 mg Rasagiline Base Delayed Release Enteric Coated Tablet

In this example, a 0.5 mg rasagiline base delayed release enteric coated tablet containing citric acid (76 mg core tablet weight) was prepared using similar steps as described in example 3a.

TABLE 3d composition of rasagiline-base delayed release enteric coated tablet

| Component | Function | Per Tablet (mg) |
|---|---|---|
| Core tablets | | |
| Rasagiline base | Drug Substance | 0.5 |
| Citric acid | Antioxidant/Stabilizer | 1.6 |
| Mannitol | Filler | 45.5 |
| Aerosil | Flowing Agent | 0.4 |
| Starch NF | Binder | 5.0 |
| Starch, Pregelatinized (Starch STA-RX 1500) | Disintegrant | 20.0 |
| Talc | Lubricant | 1.5 |
| Stearic Acid | Lubricant | 1.5 |
| Total Core Tablet Weight | | 76.0 |
| Subcoating | | |
| Pharmacoat ® 606 (Hypromellose USP) Granules | Coating Agent | 3.5 |
| Purified Water Coating Suspension | Processing Agent | |
| Eudragit ® L-30D-55 | Coating Agent | 4.0* |
| Talc USP Extra Fine | Lubricant | 1.9 |
| Triethyl citrate NF | Plasticizer | 0.8 |
| Purified Water | Processing Agent | |
| Total Tablet Weight | | 86.2 |

*Dry substance remaining on the core.

Example 4

Dissolution Results of Tablets Prepared According to Example 3a

The tablets prepared according to example 3a were tested for dissolution profile in various media according to USP procedures. The data below represents average for 4 tablets.

The % rasagiline released in the following tables is relative to a standard which is 1 mg rasagiline.

Tablet Cores:

Dissolution Profile (% rasagiline released)—0.1N HCl, 75 rpm, 37° C.

| | 10 min | 20 min | 30 min | 45 min |
|---|---|---|---|---|
| 1 | 101 | 102 | 102 | 103 |
| 2 | 105 | 106 | 105 | 106 |
| 3 | 104 | 105 | 105 | 105 |
| 4 | 106 | 106 | 107 | 107 |
| % Mean | 104 | 105 | 105 | 105 |

Dissolution Profile (% rasagiline released)—Phosphate buffer, 75 rpm, 37° C.

| | 10 min | 20 min | 30 min | 45 min |
|---|---|---|---|---|
| 1 | 98 | 99 | 99 | 99 |
| 2 | 100 | 101 | 101 | 102 |
| 3 | 99 | 100 | 100 | 101 |
| 4 | 96 | 96 | 97 | 97 |
| % Mean | 98 | 99 | 99 | 100 |
| % RSD | 1.9 | 2.0 | 2.0 | 2.2 |

Sub-Coated Tablets:
Dissolution Profile (% rasagiline released)—0.1N HCl, 75 rpm, 37° C.

|   | 10 min | 20 min | 30 min | 45 min |
|---|---|---|---|---|
| 1 | 105 | 105 | 106 | 106 |
| 2 | 109 | 109 | 109 | 109 |
| 3 | 103 | 104 | 104 | 104 |
| 4 | 103 | 104 | 103 | 104 |
| % Mean | 105 | 105 | 105 | 106 |
| % RSD | 2.5 | 2.3 | 2.3 | 2.3 |

Coated Tablets:
The dissolution profile of the coated tablets in 0.1N HCl was acceptable according to USP specification for delayed release (enteric coated) articles, 29th edition, Chapter 724, showing less than 10% release after 120 minutes.

Dissolution Profile (% rasagiline released)—Phosphate buffer pH 5.8

|   | 10 min | 20 min | 30 min | 40 min | 60 min | 90 min |
|---|---|---|---|---|---|---|
| % Mean | 0 | 0 |  | 0 | 0 | 0 |

Dissolution Profile (% rasagiline released)—Phosphate buffer pH 6.4

|   | 10 min | 20 min | 30 min | 40 min | 60 min | 90 min |
|---|---|---|---|---|---|---|
| % Mean | 0 | 35 | 93 | 96 | 96 | 96 |
| % RSD |  |  | 2.2 | 1.3 | 1.3 | 1.2 |

Dissolution Profile (% rasagiline released)—Phosphate buffer pH 6.8

|   | 10 min | 20 min | 30 min | 40 min | 60 min | 90 min |
|---|---|---|---|---|---|---|
| % Mean | 11 | 92 | 95 | 95 | 94 | 94 |
| % RSD |  | 3.7 | 1.6 | 1.6 | 1.5 | 1.6 |

Discussion:
The tablets prepared according to Example 3a do not begin the release of rasagiline at a pH lower than 6.0. At a pH of 6.8, there is a rapid release of rasagiline and within approximately 20 minutes, above 90% of the rasagiline is released from the formulation.

During the development of the formulations of the current invention, it was determined that the formulations should meet the criteria of bioequivalence to the known, immediate release rasagiline mesylate formulations (as disclosed in example 1) in a single dose bio-equivalence study in healthy subjects. These criteria include similarity of $C_{max}$ and/or $AUC_{0-t}$ (area under the curve) within the range of 80-125% within a 90% confidence interval between the new formulations and the known, immediate release formulations. The difference between the two formulations should be evident in bioequivalence studies as a difference in $t_{max}$. In other words, the mean pharmacokinetic profile of the formulations of the current invention should match substantially the mean pharmacokinetic profile of the formulations of the immediate release formulation, with the exception of the $t_{max}$ which should be greater for the delayed release formulation than for the immediate release formulation.

The reason for attempting to match the mean $C_{max}$ and $AUC_{0-t}$ of the known immediate release formulation (i.e. to formulate a delayed release formulation that is bioequivalent) is that the efficacy of the immediate release formulation has been proven, and it is likely that the efficacy of the formulation relates to its mean $C_{max}$ and/or AUC. (Arch Neurol. 2002; 59:1937-1943.)

In order to reach this target, development was directed toward delayed release enteric coated tablets having a quickly disintegrating core with an enteric coating which allows release of the rasagiline in a very specific range of pH. This specific pH range would prevent the formulation to release rasagiline in the stomach in fed condition, and would allow the formulation to release rasagiline quickly under the physiological conditions of the intestine after the stomach.

Although the tablets of example 3a were coated with an enteric coating comprising Methacrylic Acid Ethyl Acrylate copolymer, as were the compositions in PCT application publication WO 2006/014973, the tablets according to example 3a were capable of withstanding pH of 6.0 and below, whereas the composition in WO 2006/014973 were not.

The difference in dissolution profiles stems from the fact that the core's formulation contained high amount of disintegrant and the enteric film has a lower ratio of polymer to plasticizer is used in the compositions of the invention. The ratio of polymer to plasticizer between 10:1 and 2:1, and specifically 5:1, allows for enhanced in vitro dissolution profiles.

The dissolution profile of the formulation of Example 3a allows the composition to have enhanced pharmacokinetic properties, similar to the currently marketed immediate release formulations.

Example 5

Stability Results of Tablets Prepared According to Example 3a

Stability of enteric coated tablets produced using formulations containing citric acid was tested under different storage conditions. The results are summarized below.

Stability Results (Accelerated Conditions):
The dissolution profile of the enteric coated tablets in 0.1N HCl was acceptable according to USP specification for delayed release (enteric coated) articles, 29th edition, Chapter 724, showing less than 10% release after 120 minutes.

The following table shows that dissolution profile for enteric coated tablets after different period of storage.

Dissolution Profile of Coated Tablets—Phosphate buffer pH 6.8, 37° C.

| Storage Period | Dissolution Profile after Different Period of Storage (% rasagiline released) | | | | | |
|---|---|---|---|---|---|---|
| (months) | 10 min | 20 min | 30 min | 40 min | 60 min | 90 min |
| 0 | 11 | 92 | 95 | 95 | 96 | 96 |
| 1 | 28 | 95 | 96 | 96 | 97 | 97 |
| 2 | 12 | 97 | 98 | 98 | 98 | 99 |
| 3 | 35 | 101 | 103 | 103 | 104 | 104 |

The % rasagiline released in the above table is relative to a standard which is 1 mg rasagiline.

The following tables show that analytical results for different batches of the enteric coated tablets under various storage conditions.

Coated Tablets—Batch 1

| Conditions | | Assay % | Total Impurities (%) |
|---|---|---|---|
| T = 0 | | 101.5 | <DL |
| 40° C., | 1 Mo | 101.1 | <DL |
| 75RH | 2 Mo | 105.4 | 0.3% |
| | 3 Mo | 104.5 | 0.4% |
| | 4 Mo | 100.9 | 0.4% |
| 25° C., | 1 Mo | 104.7 | <DL |
| 60RH | 3 Mo | 106.2 | <DL |

Coated Tablets—Batch 2

| Conditions | | Assay % | Total Impurities (%) |
|---|---|---|---|
| T = 0 | | 98.6 | <DL |
| 40° C., | 1 Mo | 99.1 | 0.05% |
| 75RH | 2 Mo | 96.3 | 0.1% |
| | 3 Mo | 95.6 | 0.2% |
| | 4 Mo | 96.6 | 0.3% |
| 30° C., | 1 Mo | 99.8 | <DL |
| 65RH | 2 Mo | 98.4 | <DL |
| | 3 Mo | 96.5 | <DL |
| 25° C., | 1 Mo | 98.4 | <DL |
| 60RH | 2 Mo | 95.8 | <DL |
| | 3 Mo | 96.2 | <DL |

Coated Tablets—Batch 3

| Conditions | | Assay % | Total Impurities (%) |
|---|---|---|---|
| T = 0 | | 100.3 | <DL |
| 40° C., 75RH | 1 Mo | 100.3 | <DL |
| 40° C., 75RH | 2 Mo | 102.0 | <DL |
| 40° C., 75RH | 3 Mo | | <0.28 |
| 30° C., 65RH | 3 Mo | | <0.08 |
| 25° C., 60RH | 1 Mo | 101.2 | <DL |
| 25° C., 60RH | 2 Mo | 102.1 | <DL |
| 25° C., 60RH | 3 Mo | | <0.08 |

N-(2-Chloroallyl)-1(R)-aminoindan (2-Cl-AAI) Impurities

| Batch No. | 2-Cl-AAI Content, % |
|---|---|
| 1 | LT 0.00004 |
| 2 | LT 0.00004 |

Example 6a

Preparation of Rasagiline Base Delayed Release Enteric Coated Tablets

In this example, a 1 mg rasagiline base delayed release enteric coated tablet containing malic acid (117 mg core tablet weight) was prepared.

TABLE 4a composition of rasagiline-base delayed release enteric coated tablet

| Component | Function | Per Tablet (mg) |
|---|---|---|
| Core tablets | | |
| Rasagiline base | Drug Substance | 1.0 |
| Malic acid | Antioxidant/Stabilizer | 1.6 |
| Mannitol | Filler | 80.0 |
| Aerosil | Flowing Agent | 0.6 |
| Starch NF | Binder | 10.0 |
| Starch, Pregelatinized (Starch STA-RX ® 1500) | Disintegrant | 20.0 |
| Talc | Lubricant | 2.0 |
| Stearic Acid | Lubricant | 2.0 |
| Total Core Tablet Weight | | 117.2 |
| Subcoating | | |
| Pharmacoat ® 606 (Hypromellose USP) Granules | Coating Agent | 4.8 |
| Purified Water Coating Suspension | Processing Agent | |
| Eudragit ® L-30D-55 | Coating Agent | 6.25* |
| Talc USP Extra Fine | Lubricant | 3.1 |
| Triethyl citrate NF | Plasticizer | 1.25 |
| Purified Water | Processing Agent | |
| Total Tablet Weight | | 132.6 |

*Dry substance remaining on the core.

I. Dry Mixing:

Mannitol, half amount of Aerosil, Starch Pregelatinized and starch NF are placed into a high shear granulating mixer and are premixed for 1 minute mixing at mixer speed I, followed by 1 minute mixing at mixer speed II and chopper II.

II. Wet Granulation:

Malic acid solution was prepared using malic acid in purified water in the ratio of approximately 1:10.6 to 1:6.

Rasagiline Base was added with stirring for approximately 15 minutes. The stirring was continued until a clear solution was observed.

The solution was added into a high shear granulating mixer and was mixed for approximately 2 minute mixing at mixer speed II and chopper II. An extra amount of water was added into the high shear granulating mixer, and the solution was mixed for two more minutes at mixer speed II and chopper II.

The wet granulate was discharged to a fluid bed dryer trolley at mixer speed I.

III. Fluid Bed Drying:

The material was dried in a fluid bed dryer under inlet air temperature of 45° C. (40° to 50° C.) and outlet air temperature of maximum 37-38° C.

IV. Milling:

The dry granulate was milled with the residual amount of Aerosil through an oscillating granulator with screen 0.6 mm into storage container.

The milled granulate is weighed.

V. Final Blending:
1. Stearic Acid and Talc were sieved through a 50 mesh screen and transferred to the Y-cone or Bin.
2. The mixture was mixed for 5 minutes.
3. The final blend was stored in a container using an inner transparent polyethylene bag and an outer black polyethylene bag. Two Silica gel pillows were placed between the two polyethylene bags.
4. Samples were taken for a Blend Uniformity test.

VI. Tablet Compression:

The compressing tablet machine was set up with the designated punches 6.0 mm. The diameter of the punch may change ±10%.

The in-process control testing for tablets includes average weight, individual weight, thickness, hardness, friability and disintegration.

In process control specifications for the Rasagiline Base DR 1 mg tablet cores are:

| Parameter | Minimum | Target | Maximum |
|---|---|---|---|
| Avarage weight (mg) | 111 | 117 (121 Actual) | 123 |
| Individual weight (mg) | 111 | 117 | 123 |
| Tickness (mm) | 3.3 | 3.6 (3.7 Actual) | 3.9 |
| Hardness (SCU) | 7 | 9 (10 Actual) | 11 |
| Friability (%) | — | — | 1.0 |
| Disintegration (minutes) | — | — | 5 |

The tablet cores are weighed and the percentage yield is calculated.

VII. Sub-Coating:

Tablet cores were first coated with hypromellose (Pharmacoat 606) as a pre-coating, followed by Methacrylic Acid-Methyl Methacrylate Copolymer [1:1] (30% dispersion of Eudragit® L100-55) to prevent any possible interaction between the Rasagiline base in the core and the Eudragit L polymer.

1. Preparation of Pharmacoat 606 solution:
   Pharmacoat 606 (hypromellose USP) solution was prepared using Pharmacoat 606 in purified water in a weight ratio of 1:10.
2. Pre heating:
   The tablet cores are place in an Ohara Coater coating pan the tablets was heated under inlet air temperature of 50° C. (45° to 55° C.) and outlet air temperature of 40° to 50° C.
3. Spraying process:
   The tablet cores were sprayed with solution in an Ohara Coater coating pan. The inlet air temperature was 50° C. (in the range of 40-50° C.); the outlet air temperature was in range of 30-40° C. The pan speed was set to 16 rpm in the range of 14-18 rpm; spraying rate was 15-35 gr/min. The tablets were dried for 1 hour with inlet air temperature of 45° C. (in the range of 40-50° C.).

VIII. Enteric Coating:

The Rasagiline subcoated drug product tablet formulation described in previous section was used for the enteric coated.

1. Preparation of Eudragit® L100-55 dispersion:
   Triethyl citrate was mixed with the water for 15 min. The Talc Extra fine was added into the Triethyl citrate and water dispersion in an Ultraturax within 10 minutes. Eudragit® L100-55 was added to Triethyl citrate/talc dispersion, filtered and stirred to the continuation of the process.
2. Pre heating:
   The tablet cores are place in an Ohara Coater coating pan the tablets was heated under inlet air temperature of 50° C. (45° to 55° C.) and outlet air temperature of 45° C. (40° to 50° C.).
2. Spraying process:
   The tablets were sprayed with the dispersion in an Ohara coater pan. The inlet air temperature was 45° C.; the outlet air temperature was 35° C. (in range of 30-40° C.). The pan speed was set to 16 rpm (in the range of 14-18 rpm), and the spraying rate was 5-20 gr/min. The tablets were dried for 2 hours; with inlet air temperature of 50° C. (in the range of 45-55° C.), on minimum pan speed.

Example 6b

Preparation of 1 mg Rasagiline Base Delayed Release Enteric Coated Tablet

In this example, a 1 mg rasagiline base delayed release enteric coated tablet containing malic acid (76 mg core tablet weight) was prepared using similar steps as described in example 6a.

TABLE 4b composition of rasagiline-base delayed release enteric coated tablet

| Component | Function | Per Tablet (mg) |
|---|---|---|
| Core tablets | | |
| Rasagiline base | Drug Substance | 1.0 |
| Malic acid | Antioxidant/Stabilizer | 1.6 |
| Mannitol | Filler | 45.0 |
| Aerosil | Flowing Agent | 0.4 |
| Starch NF | Binder | 5.0 |
| Starch, Pregelatinized (Starch STA-RX 1500) | Disintegrant | 20.0 |
| Talc | Lubricant | 1.5 |
| Stearic Acid | Lubricant | 1.5 |
| Total Core Tablet Weight | | 76.0 |
| Subcoating | | |
| Pharmacoat ® 606 (Hypromellose USP) Granules | Coating Agent | 3.5 |
| Purified Water | Processing Agent | |
| Coating Suspension | | |
| Eudragit ® L-30D-55 | Coating Agent | 4.0* |
| Talc USP Extra Fine | Lubricant | 1.9 |
| Triethyl citrate NF | Plasticizer | 0.8 |
| Purified Water | Processing Agent | |
| Total Tablet weight | | 86.2 |

*Dry substance remaining on the core.

Example 6c

Preparation of 0.5 mg Rasagiline Base Delayed Release Enteric Coated Tablet

In this example, a 0.5 mg rasagiline base delayed release enteric coated tablet containing malic acid (117 mg core tablet weight) was prepared using similar steps as described in example 6a.

TABLE 4c composition of rasagiline-base delayed release enteric coated tablet

| Component | Function | Per Tablet (mg) |
|---|---|---|
| Core tablets | | |
| Rasagiline base | Drug Substance | 0.5 |
| Malic acid | Antioxidant/Stabilizer | 1.6 |
| Mannitol | Filler | 80.34 |
| Aerosil | Flowing Agent | 0.6 |
| Starch NF | Binder | 10.0 |
| Starch, Pregelatinized (Starch STA-RX 1500) | Disintegrant | 20.0 |
| Talc | Lubricant | 2.0 |
| Stearic Acid | Lubricant | 2.0 |
| Total Core Tablet Weight | | 117.0 |
| Subcoating | | |
| Pharmacoat ® 606 (Hypromellose USP) Granules | Coating Agent | 4.8 |
| Purified Water Coating Suspension | Processing Agent | |
| Eudragit ® L-30D-55 | Coating Agent | 6.25* |
| Talc USP Extra Fine | Lubricant | 3.1 |
| Triethyl citrate NF | Plasticizer | 1.25 |
| Purified Water | Processing Agent | |
| Total Tablet weight | | 132.4 |

*Dry substance remaining on the core.

Example 6d

Preparation of 0.5 mg Rasagiline Base Delayed Release Enteric Coated Tablet

In this example, a 0.5 mg rasagiline base delayed release enteric coated tablet containing malic acid (76 mg core tablet weight) was prepared using similar steps as described in example 6a.

TABLE 4d composition of rasagiline-base delayed release enteric coated tablet

| Component | Function | Per Tablet (mg) |
|---|---|---|
| Core tablets | | |
| Rasagiline base | Drug Substance | 0.5 |
| Malic acid | Antioxidant/Stabilizer | 1.6 |
| Mannitol | Filler | 45.5 |
| Aerosil | Flowing Agent | 0.4 |
| Starch NF | Binder | 5.0 |
| Starch, Pregelatinized (Starch STA-RX 1500) | Disintegrant | 20.0 |
| Talc | Lubricant | 1.5 |
| Stearic Acid | Lubricant | 1.5 |
| Total Core Tablet Weight | | 76.0 |
| Subcoating | | |
| Pharmacoat ® 606 (Hypromellose USP) Granules | Coating Agent | 3.5 |
| Purified Water Coating Suspension | Processing Agent | |
| Eudragit ® L-30D-55 | Coating Agent | 4.0* |
| Talc USP Extra Fine | Lubricant | 1.9 |
| Triethyl citrate NF | Plasticizer | 0.8 |
| Purified Water | Processing Agent | |
| Total Tablet weight | | 86.2 |

*Dry substance remaining on the core.

Example 7

Dissolution Results of Tablets According to Example 6a

The tablets prepared according to example 6a were tested for dissolution profile in various media according to USP procedures. The data below represents the average for 4 tablets.

The dissolution profile of the enteric coated tablets in 0.1N HCl was acceptable according to USP specification for delayed release (enteric coated) articles, 29th edition, Chapter 724, showing less than 10% release after 120 minutes.

Example 8

Stability Results of Tablets Prepared According to Example 6a

Stability of enteric coated tablets produced using formulations containing citric acid was tested under different storage conditions. The results are summarized below.

Stability Results (Accelerated Conditions):

The dissolution profile of the enteric coated tablets in 0.1N HCl was acceptable according to USP specification for delayed release (enteric coated) articles, 29th edition, Chapter 724, showing less than 10% release after 120 minutes.

The following table shows that dissolution profile for enteric coated tablets after different period of storage.

Dissolution Profile of Coated Tablets—Phosphate buffer pH 6.8, 37° C.

| Storage Period | Dissolution Profile after Different Period of Storage (% rasagiline released) | | | | | |
|---|---|---|---|---|---|---|
| (months) | 10 min | 20 min | 30 min | 40 min | 60 min | 90 min |
| 1 | 0 | 89 | 93 | 94 | 94 | 94 |
| 2 | 0 | 92 | 93 | 93 | 94 | 94 |

The % rasagiline released in the above table is relative to a standard which is 1 mg rasagiline.

The following tables show that analytical results for tablets under various storage conditions.

Tablet Cores:

| Conditions | | Assay (%) | Total Impurities |
|---|---|---|---|
| T = 0 | | 101.2 | <DL |
| 40° C., 75RH | 1 Mo | 101.1 | 0.1 |
| | 2 Mo | 98.3 | 0.3 |
| | 3 Mo | 93.3 | 0.5 |
| | 4 Mo | 93.1 | 0.4 |
| 30° C., 65RH | 1 Mo | 101.4 | <DL |
| | 2 Mo | 101.9 | <QL |
| | 3 Mo | 98.3 | <QL |
| 25° C., 60RH | 1 Mo | 101.5 | <DL |
| | 2 Mo | 102.0 | <QL |
| | 3 Mo | 100.3 | <QL |

Enteric Coated Tablets:

| Conditions | | Assay % | Total Impurities |
|---|---|---|---|
| T = 0 | | 98.2 | <QL |
| 40° C., 75RH | 1 Mo | 100.5 | 0.2 |
| | 2 Mo | 96.4 | 0.3 |
| | 3 Mo | 96.6 | 0.5 |
| 30° C., 65RH | 1 Mo | 98.2 | <QL |
| | 2 Mo | 100.2 | <QL |
| | 3 Mo | 101.0 | 0.1 |
| 25° C., 60RH | 1 Mo | 101.5 | <QL |
| | 2 Mo | 96.7 | <QL |
| | 3 Mo | 99.5 | <QL |

N-(2-Chloroallyl)-1(R)-aminoindan (2-Cl-AAI) Impurities

| Batch No | 2-Cl-AAI Content, % |
|---|---|
| 1 | <0.00004 |

Example 9

Preparation of Rasagiline Base Tablet Cores (with Citric Acid)

| Raw material | mg/tablet | Percentage |
|---|---|---|
| Part I, Granulation solution | | |
| Citric acid | 1.6 | 2.0 |
| Rasagiline base | 1 | 1.25 |
| Purified Water | 12.35 | 15.44 |
| Part II | | |
| Mannitol | 48.5 | 60.63 |
| Aerosil 200 | 0.18 | 0.22 |
| Starch NF/BP | 6.1 | 7.62 |
| Pregelatinized starch NF/Ph. Eur | 20.0 | 25.0 |
| Part III | | |
| Aerosil 200 | 0.18 | 0.22 |
| Part IV | | |
| Stearic acid | 1.22 | 1.52 |
| Talc | 1.22 | 1.52 |
| Total: | 80.0 | 100 |

The above composition can also be used to prepare rasagiline base tablets with malic acid by replacing the citric acid with the same amount of malic acid.

Calculated Amounts of External Excipients in Accordance with Actual Amount of Granulate:

| mg/tablet | Raw material | Percentage |
|---|---|---|
| | Part III | |
| 0.18 | Granulate Aerosil 200 | 0.22 |
| | Part IV | |
| 1.22 | Stearic acid | 1.52 |
| 1.22 | Talc | 1.52 |

I. Granulation Solution Preparation:
1. Weigh 80% of needed amount of Purified water into glass.
2. Weigh into the same glass Citric acid.
3. Insert stirrer into the glass and start to stir up to complete solubility about 5-10 minutes.
4. Weigh Rasagiline base and add it into the obtained Citric acid solution.
5. Continue stirring about 30 minutes to complete solubility of API.

II. Granulation Preparation:
1. Weigh Mannitol, Aerosil 200, Starch and Pregelatinized starch and transfer all excipients to Diosna P-6 (Diosna) and mix for 1 minute with Mixer I (270 rpm).
2. Mix the excipient for 1 addition minute with Mixer I (270 rpm) and Chopper I (1500 rpm)
3. Add Granulation solution into the Diosna P-6(Diosna) and mix for 2 minutes with Mixer II (540 rpm) and Chopper II (2200 rpm).
4. Clean glass after granulation solution with 46.563 g of Purified water and add it into the Diosna P-6 (Diosna).
5. Mix for 2 minutes with Mixer II (540 rpm) and Chopper II (2200 rpm).
6. Transfer obtained granulate into the Glatt 1.1 (Fluid Bed) for drying at 37° C. inlet air up to L.O.D. NMT 1.5%.

Conditions of Drying:
Inlet: Min.—35° C.; Target—50° C.; Max.—55° C.
Outet: Product temperature—37° C.
Flow: Min.—25; Target—60; Max.—1000

III. Milling:
Mill granulate through 0.6 mm sieve using Frewitt.

IV. Final Blend:
1. Weigh obtained amount of granulate.
2. Calculate amounts of Aerosil 200, Stearic acid and Talc in accordance with actual granulation weight.
3. Screen Aerosil 200 through 50 mesh sieve.
4. Weigh needed amount of Aerosil 200 after sieving.

5. Transfer milled granulate and Aerosil 200 after sieving into the Y-cone.
6. Mix for 2 minutes.
7. Weigh Stearic acid and Talc.
8. Screen these excipients through 50 mesh sieve.
9. Transfer them into the Y-cone.
10. Mix for 5 minutes.

V. Tablet Compression:

Machine: Sviac
Diameter of punch: 5.0 mm (it may be changed ±10%)
Tablet weight—80 mg±5%
Hardness: 3-7 kP
Friability: Not More Than 1%
Disintegration: Not More Than 5 minutes Example 10

Preparation of Rasagiline Base Tablet Cores (with Malic Acid)

| Raw material | mg/tablet | Percentage |
|---|---|---|
| Part I, Granulation solution | | |
| Malic acid | 1.6 | 3.72 |
| Rasagiline base | 1 | 2.33 |
| Part II | | |
| Mannitol | 25.8 | 60.0 |
| Aerosil 200 | 0.1 | 0.24 |
| Starch NF/BP | 3.0 | 6.98 |
| Pregelatinized starch NF/Ph. Eur | 10.0 | 23.26 |
| Part III | | |
| Aerosil 200 | 0.1 | 0.23 |
| Part IV | | |
| Stearic acid | 0.7 | 1.63 |
| Talc | 0.7 | 1.63 |
| Total: | 43.0 | 100 |

The above composition can also be used to prepare rasagiline base tablets with citric acid by replacing the malic acid with the same amount of citric acid.

I. Granulation Solution Preparation.
1. weigh 80% of needed amount of Purified water into glass.
2. Weigh Malic acid and add it into the same glass.
3. Insert stirrer into the glass and start to stir up to complete solubility about 5-10 minutes.
4. Weigh Rasagiline base and add it into the obtained Malic acid solution.
5. Continue stirring about 30 minutes to complete solubility of API.

II. Granulation Preparation.
1. Weigh Mannitol, Aerosil 200, Starch and Pregelatinized starch and transfer all excipients to Diosna P-10 (Diosna) and mix for 1 minute with Mixer I.
2. Mix the excipient for 1 addition minute with Mixer I and Chopper I rpm.
3. Add granulation solution into the Diosna P-10 (Diosna) and mix for 2 minutes with Mixer II and Chopper II.
4. Add additional Purified Water into the Diosna P-10 (Diosna) and mix for 2 minutes with Mixer II, and Chopper II.
5. Transfer obtained granulate into the Glatt 5 (Fluid Bed) for drying at 37° C. inlet air up to L.O.D. NMT 1.5%.

Conditions of drying:
Inlet: Min.—35° C.; Target—50° C.; Max.—55° C.
Outet: Product temperature—37° C.

III. Milling.
Weigh and add Aerosil 200 to granulate and milled granulate through 0.6 mm sieve using Frewitt.

IV. Final Blend.
1. Weigh Stearic acid and Talc.
2. Screen the excipients through 50 mesh sieve.
3. Transfer milled granulate and sieved Stearic acid and Talc into the Y-cone.
4. Mix for 5 minutes.

V. Tablet Compression:
Machine: Sviac
Diameter of punch: 4.0 mm (it may be changed ±10%)
Tablet weight—43 mg±5%
Hardness: 3-5 kP
Friability: Not More Than 1%
Disintegration: Not More Than 5 minutes Example 11

Preparation of Rasagiline Base Tablet Cores (Citric and Malic Acids together)

| Raw material | Mg/tablet | Percentage |
|---|---|---|
| Part I, Granulation solution | | |
| Citric acid | 0.8 | 0.68 |
| Malic acid | 0.8 | 0.68 |
| Rasagiline base | 1.0 | 0.85 |
| Part II | | |
| Mannitol | 79.8 | 68.2 |
| Aerosil 200 | 0.3 | 0.26 |
| Starch NF/BP | 10.0 | 8.55 |
| Pregelatinized starch NF/Ph. Eur | 20.0 | 17.09 |
| Part III | | |
| Aerosil 200 | 0.3 | 0.26 |
| Part IV | | |
| Stearic acid | 2.0 | 1.71 |
| Talc | 2.0 | 1.71 |
| Total: | 117.0 | 100 |

Calculated Amounts of External Excipients in Accordance with Actual amount of Granulate

| Raw material | mg/tablet | Percentage |
|---|---|---|
| Part III | | |
| Granulate Aerosil 200 | 0.3 | 0.26 |
| Part IV | | |
| Stearic acid | 2.0 | 1.71 |
| Talc | 2.0 | 1.71 |

I. Granulation Solution 1 Preparation.
1. Weigh 80% of needed amount of Purified water into glass.
2. Weigh into the same glass Citric acid.
3. Insert stirrer into the glass and start to stir up to complete solubility about 5-10 minutes.
4. Weigh Rasagiline base and add it into the obtained Citric acid solution.
5. Continue stirring about 30 minutes to complete solubility of API.

II. Granulation Solution 2 Preparation.
1. Weigh 20% of needed amount of Purified water into the glass.
2. Add into this glass weighed amount of Malic acid.
3. Insert stirrer into the glass and start to stir up to complete solubility about 5-10 minutes.

III. Granulation Preparation.
1. Weigh Mannitol, Aerosil 200, Starch and Pregelatinized starch and transfer all excipients to Diosna P-6 (Diosna) and mix for 1 minute with Mixer I (270 rpm).
2. Mix the excipient for 1 addition minute with Mixer I (270 rpm) and Chopper I (1500 rpm)
3. Add Granulation solution 1 into the Diosna P-6 (Diosna) and mix for 2 minutes with Mixer II (540 rpm) and Chopper II (2200 rpm).
4. Clean glass after granulation solution 1 with Granulation solution 2 and add it into the Diosna P-6(Diosna).
5. Mix for 2 minutes with Mixer II (540 rpm) and Chopper II (2200 rpm).
6. Transfer obtained granulate into the Glatt 1.1 (Fluid Bed) for drying at 37° C. inlet air up to L.O.D. NMT 1.5%.

Conditions of Drying:
Inlet: Min.—35° C.; Target—50° C.; Max—55° C.
Outet: Product temperature—37° C.
Flow: Min.—25; Target—60; Max—1000

IV. Milling:
Mill obtained granulate through 0.6 mm sieve using Frewitt.

V. Final Blend:
1. Weigh obtained amount of granulate.
2. Calculate amounts of Aerosil 200, Stearic acid and Talc in accordance with actual granulation weight.
3. Screen Aerosil 200 through 50 mesh sieve.
4. Weigh needed amount of Aerosil 200 after sieving.
5. Transfer milled granulate and Aerosil 200 after sieving into the Y-cone.
6. Mix for 2 minutes.
7. Weigh Stearic acid and Talc.
8. Screen these excipients through 50 mesh sieve.
9. Transfer them into the Y-cone.
10. Mix for 5 minutes.

VI. Tablet Compression
Machine: Sviac
Diameter of punch: 6.0 mm (it may be changed ±10%)
Tablet weight—117 mg±5%
Hardness: 6-8 kP
Friability: Not More Than 1%
Disintegration: Not More Than 5 minutes VII. Subcoating:

| Mg/tablet | Raw material |
|---|---|
| 4.8 | Pharmacoat 606 (Hypromellose USP) |

Equipment: O'HARA, Peristaltic Pump

1. Preparation of Sub-coating solution:
Pharmacoat 606 (hypromellose USP) was added into the vessel with 1510 g of Purified water and mixed for 30 minutes using stirrer.

2. Preheating:
The core tablets were placed into the Pan 2.5 kg of O'HARA Coater and preheated:
Inlet air temperature—50° C. (45° to 55° C.)
Outlet air temperature—45° C. (40° to 50° C.).
Difference pressure——50 Pa 3. Spraying process (the process was continued till desired tablet weight was achieved):
Sub-coating solution was sprayed on the preheated core tablets at the following conditions:
Number of spray guns—1
Nozzle bore—1 mm
Distance tablet bed/spray gun—15 cm
Pan speed 10 rpm (8-12 rpm)
Inlet air temperature—50° C. (45° to 55° C.)
Outlet air temperature—35° C. (30° to 40° C.)
Spraying rate—10-20 g/min
Difference pressure——50 Pa
Atomizing air pressure—30 Psi
Pattern air pressure—30 Psi 4. Drying process:
Inlet air temperature—45° C. (40° to 50° C.)
Outlet air temperature—40° C.-50° C.
Pan speed—5 rpm Jogging
Drying time—60 min Example 12a Rasagiline Base 0.5 mg Enteric Coated Optional Formulations—with Citric Acid This example describes 0.5 mg rasagiline base formulations with variations in the amount of citric acid and other excipients. These formulations have a dissolution and pharmacokinetic profile ($C_{max}$ and AUC) resembling that of example 1.

| Component | Function | Per Tablet (mg) | Per Tablet (mg) | Per Tablet (mg) | Per Tablet (mg) |
|---|---|---|---|---|---|
| Core tablets | | | | | |
| Rasagiline base | Drug Substance | 0.5 | 0.5 | 0.5 | 0.5 |
| Citric acid | Antioxidant | 1.6 or 0.8 | 1.6 or 0.8 | 1.6 or 0.8 | 1.6 or 0.8 |
| Mannitol | Filler | 45.5 | 68.3 | 50.5 | 80.3 |
| Aerosil | Flowing Agent | 0.4 | 0.6 | 0.4 | 0.6 |
| Starch NF | Binder | 5.0 | 10.0 | 5.0 | 10 |
| Starch, Pregelatinized (Starch STA-RX 1500) | Disintegrant | 20.0 | 20.0 | 15.0 | 20.0 |
| Talc | Lubricant | 1.5 | 2.0 | 1.5 | 2.0 |
| Stearic Acid | Lubricant | 1.5 | 2.0 | 1.5 | 2.0 |
| Total Core Tablet Weight | | 76.0 (+/−10%) | 105.0 (+/−10%) | 76.0 (+/−10%) | 117.0 (+/−10%) |
| Subcoating | | | | | |
| Pharmacoat 606 (Hypromellose USP) Granules | Coating Agent | 3.5 (+/−10%) | 4.8 (+/−10%) | 3.5 (+/−10%) | 4.8 (+/−10%) |
| Purified Water Coating Suspension | Processing Agent | | | | |
| Eudragit L-30D-55 | Coating Agent | 4.0 (+/−10%) | 4.0 (+/−10%) | 4.0 (+/−10%) | 6.25 (+/−10%) |
| Talc USP Extra Fine | Lubricant | 1.9 (+/−10%) | 1.9 (+/−10%) | 1.9 (+/−10%) | 3.1 (+/−10%) |
| Triethyl citrate NF | Plasticizer | 0.8 (+/−10%) | 0.8 (+/−10%) | 0.8 (+/−10%) | 1.25 (+/−10%) |
| Purified Water | Processing Agent | | | | |

Example 12b

Rasagiline Base 1 mg Enteric Coated Optional Formulations—with Citric Acid

This example describes 1 mg rasagiline base formulations with variations in the amount of citric acid and other excipients. These formulations have a dissolution and pharmacokinetic profile ($C_{max}$ and AUC) resembling that of example 1.

| Component | Function | Per Tablet (mg) | Per Tablet (mg) | Per Tablet (mg) | Per Tablet (mg) |
|---|---|---|---|---|---|
| Core tablets | | | | | |
| Rasagiline base | Drug Substance | 1.0 | 1.0 | 1.0 | 1.0 |
| Citric acid | Antioxidant | 1.6 or 0.8 | 1.6 or 0.8 | 1.6 or 0.8 | 1.6 or 0.8 |
| Mannitol | Filler | 45.0 | 67.8 | 50.0 | 79.8 |
| Aerosil | Flowing Agent | 0.4 | 0.6 | 0.4 | 0.6 |
| Starch NF | Binder | 5.0 | 10.0 | 5.0 | 10.0 |
| Starch, Pregelatinized (Starch STA-RX 1500) | Disintegrant | 20.0 | 20.0 | 15.0 | 20.0 |
| Talc | Lubricant | 1.5 | 2.0 | 1.5 | 2.0 |
| Stearic Acid | Lubricant | 1.5 | 2.0 | 1.5 | 2.0 |
| Total Core Tablet Weight | | 76.0 (+/−10%) | 105.0 (+/−10%) | 76.0 (+/−10%) | 117.0 (+/−10%) |
| Subcoating | | | | | |
| Pharmacoat 606 (Hypromellose USP) Granules | Coating Agent | 3.5 (+/−10%) | 4.8 (+/−10%) | 3.5 (+/−10%) | 4.8 (+/−10%) |
| Purified Water Coating | Processing Agent | | | | |

-continued

| Component | Function | Per Tablet (mg) | Per Tablet (mg) | Per Tablet (mg) | Per Tablet (mg) |
|---|---|---|---|---|---|
| Suspension | | | | | |
| Eudragit L-30D-55 | Coating Agent | 4.0 (+/−10%) | 4.0 (+/−10%) | 4.0 (+/−10%) | 6.25 (+/−10%) |
| Talc USP Extra Fine | Lubricant | 1.9 (+/−10%) | 1.9 (+/−10%) | 1.9 (+/−10%) | 3.1 (+/−10%) |
| Triethyl citrate NF | Plasticizer | 0.8 (+/−10%) | 0.8 (+/−10%) | 0.8 (+/−10%) | 1.25 (+/−10%) |
| Purified Water | Processing Agent | | | | |

Example 13a

Rasagiline Base 0.5 mg Enteric Coated Optional Formulations—with Malic Acid

This example describes 0.5 mg rasagiline base formulations with variations in the amount of malic acid and other excipients. These formulations have a dissolution and pharmacokinetic profile ($C_{max}$ and AUC) resembling that of example 1.

| Component | Function | Per Tablet (mg) | Per Tablet (mg) | Per Tablet (mg) | Per Tablet (mg) |
|---|---|---|---|---|---|
| Core tablets | | | | | |
| Rasagiline base | Drug Substance | 0.5 | 0.5 | 0.5 | 0.5 |
| Malic acid | Antioxidant | 1.6 or 0.8 | 1.6 or 0.8 | 1.6 or 0.8 | 1.6 or 0.8 |
| Mannitol | Filler | 45.5 | 68.3 | 50.5 | 80.3 |
| Aerosil | Flowing Agent | 0.4 | 0.6 | 0.4 | 0.6 |
| Starch NF | Binder | 5.0 | 10.0 | 5.0 | 10 |
| Starch, Pregelatinized (Starch STA-RX 1500) | Disintegrant | 20.0 | 20.0 | 15.0 | 20.0 |
| Talc | Lubricant | 1.5 | 2.0 | 1.5 | 2.0 |
| Stearic Acid | Lubricant | 1.5 | 2.0 | 1.5 | 2.0 |
| Total Core Tablet Weight | | 76.0 (+/−10%) | 105.0 (+/−10%) | 76.0 (+/−10%) | 117.0 (+/−10%) |
| Subcoating | | | | | |
| Pharmacoat 606 (Hypromellose USP) Granules | Coating Agent | 3.5 (+/−10%) | 4.8 (+/−10%) | 3.5 (+/−10%) | 4.8 (+/−10%) |
| Purified Water | Processing Agent | | | | |
| Coating Suspension | | | | | |
| Eudragit L-30D-55 | Coating Agent | 4.0 (+/−10%) | 4.0 (+/−10%) | 4.0 (+/−10%) | 6.25 (+/−10%) |
| Talc USP Extra Fine | Lubricant | 1.9 (+/−10%) | 1.9 (+/−10%) | 1.9 (+/−10%) | 3.1 (+/−10%) |
| Triethyl citrate NF | Plasticizer | 0.8 (+/−10%) | 0.8 (+/−10%) | 0.8 (+/−10%) | 1.25 (+/−10%) |
| Purified Water | Processing Agent | | | | |

Example 13b

Rasagiline Base 1 mg Enteric Coated Optional Formulations—with Malic Acid

This example describes 1 mg rasagiline base formulations with variations in the amount of malic acid and other excipients. These formulations have a dissolution and pharmacokinetic profile ($C_{max}$ and AUC) resembling that of example 1.

| Component | Function | Per Tablet (mg) | Per Tablet (mg) | Per Tablet (mg) | Per Tablet (mg) |
|---|---|---|---|---|---|
| Core tablets | | | | | |
| Rasagiline base | Drug Substance | 1.0 | 1.0 | 1.0 | 1.0 |
| Malic acid | Antioxidant | 1.6 or 0.8 | 1.6 or 0.8 | 1.6 or 0.8 | 1.6 or 0.8 |
| Mannitol | Filler | 45.0 | 67.8 | 50.0 | 79.8 |
| Aerosil | Flowing Agent | 0.4 | 0.6 | 0.4 | 0.6 |
| Starch NF | Binder | 5.0 | 10.0 | 5.0 | 10.0 |
| Starch, Pregelatinized (Starch STA-RX 1500) | Disintegrant | 20.0 | 20.0 | 15.0 | 20.0 |
| Talc | Lubricant | 1.5 | 2.0 | 1.5 | 2.0 |
| Stearic Acid | Lubricant | 1.5 | 2.0 | 1.5 | 2.0 |
| Total Core Tablet Weight | | 76.0 (+/−10%) | 105.0 (+/−10%) | 76.0 (+/−10%) | 117.0 (+/−10%) |
| Subcoating | | | | | |
| Pharmacoat 606 (Hypromellose USP) Granules | Coating Agent | 3.5 (+/−10%) | 4.8 (+/−10%) | 3.5 (+/−10%) | 4.8 (+/−10%) |
| Purified Water | Processing Agent | | | | |
| Coating Suspension | | | | | |
| Eudragit L-30D-55 | Coating Agent | 4.0 (+/−10%) | 4.0 (+/−10%) | 4.0 (+/−10%) | 6.25 (+/−10%) |
| Talc USP Extra Fine | Lubricant | 1.9 (+/−10%) | 1.9 (+/−10%) | 1.9 (+/−10%) | 3.1 (+/−10%) |
| Triethyl citrate NF | Plasticizer | 0.8 (+/−10%) | 0.8 (+/−10%) | 0.8 (+/−10%) | 1.25 (+/−10%) |
| Purified Water | Processing Agent | | | | |

Example 14a

Rasagiline Base 0.5 mg Enteric Coated Optional Formulations—with both Citric and Malic Acid This example describes 0.5 mg rasagiline base formulations with variations in the amount of citric acid, malic acid, and other excipients. These formulations have a dissolution and pharmacokinetic profile ($C_{max}$ and AUC) resembling that of example 1.

| Component | Function | Per Tablet (mg) | Per Tablet (mg) | Per Tablet (mg) | Per Tablet (mg) |
|---|---|---|---|---|---|
| Core tablets | | | | | |
| Rasagiline base | Drug Substance | 0.5 | 0.5 | 0.5 | 0.5 |
| Malic acid | Antioxidant | 0.8 or 0.4 | 0.8 or 0.4 | 0.8 or 0.4 | 1.6 or 0.8 |
| Citric acid | Antioxidant | 0.8 or 0.4 | 0.8 or 0.4 | 0.8 or 0.4 | 1.6 or 0.8 |
| Mannitol | Filler | 45.5 | 68.3 | 50.5 | 80.3 |
| Aerosil | Flowing Agent | 0.4 | 0.6 | 0.4 | 0.6 |
| Starch NF | Binder | 5.0 | 10.0 | 5.0 | 10.0 |
| Starch, Pregelatinized (Starch STA-RX 1500) | Disintegrant | 20.0 | 20.0 | 15.0 | 20.0 |
| Talc | Lubricant | 1.5 | 2.0 | 1.5 | 2.0 |
| Stearic Acid | Lubricant | 1.5 | 2.0 | 1.5 | 2.0 |
| Total Core Tablet Weight | | 76.0 (+/−10%) | 105.0 (+/−10%) | 76.0 (+/−10%) | 117.0 (+/−10%) |

-continued

| Component | Function | Per Tablet (mg) | Per Tablet (mg) | Per Tablet (mg) | Per Tablet (mg) |
|---|---|---|---|---|---|
| Subcoating | | | | | |
| Pharmacoat 606 (Hypromellose USP) Granules | Coating Agent | 3.5 (+/−10%) | 4.8 (+/−10%) | 3.5 (+/−10%) | 4.8 (+/−10%) |
| Purified Water Coating Suspension | Processing Agent | | | | |
| Eudragit L-30D-55 | Coating Agent | 4.0 (+/−10%) | 4.0 (+/−10%) | 4.0 (+/−10%) | 6.25 (+/−10%) |
| Talc USP Extra Fine | Lubricant | 1.9 (+/−10%) | 1.9 (+/−10%) | 1.9 (+/−10%) | 3.1 (+/−10%) |
| Triethyl citrate NF | Plasticizer | 0.8 (+/−10%) | 0.8 (+/−10%) | 0.8 (+/−10%) | 1.25 (+/−10%) |
| Purified Water | Processing Agent | | | | |

Example 14b

Rasagiline Base 1 mg Enteric Coated Optional Formulations—with both Citric and Malic Acid This example describes 1 mg rasagiline base formulations with variations in the amount of citric acid, malic acid, and other excipients. These formulations have a dissolution and pharmacokinetic profile ($C_{max}$ and AUC) resembling that of example 1.

| Component | Function | Per Tablet (mg) | Per Tablet (mg) | Per Tablet (mg) | Per Tablet (mg) |
|---|---|---|---|---|---|
| Core tablets | | | | | |
| Rasagiline base | Drug Substance | 1.0 | 1.0 | 1.0 | 1.0 |
| Malic acid | Antioxidant | 0.8 or 0.4 | 0.8 or 0.4 | 0.8 or 0.4 | 1.6 or 0.8 |
| Citric acid | Antioxidant | 0.8 or 0.4 | 0.8 or 0.4 | 0.8 or 0.4 | 1.6 or 0.8 |
| Mannitol | Filler | 45.0 | 67.8 | 50.0 | 79.8 |
| Aerosil | Flowing Agent | 0.4 | 0.6 | 0.4 | 0.6 |
| Starch NF | Binder | 5.0 | 10.0 | 5.0 | 10.0 |
| Starch, Pregelatinized (Starch STA-RX 1500) | Disintegrant | 20.0 | 20.0 | 15.0 | 20.0 |
| Talc | Lubricant | 1.5 | 2.0 | 1.5 | 2.0 |
| Stearic Acid | Lubricant | 1.5 | 2.0 | 1.5 | 2.0 |
| Total Core Tablet Weight | | 76.0 (+/−10%) | 105.0 (+/−10%) | 76.0 (+/−10%) | 117.0 (+/−10%) |
| Subcoating | | | | | |
| Pharmacoat 606 (Hypromellose USP) Granules | Coating Agent | 3.5 (+/−10%) | 4.8 (+/−10%) | 3.5 (+/−10%) | 4.8 (+/−10%) |
| Purified Water Coating Suspension | Processing Agent | | | | |
| Eudragit L-30D-55 | Coating Agent | 4.0 (+/−10%) | 4.0 (+/−10%) | 4.0 (+/−10%) | 6.25 (+/−10%) |
| Talc USP Extra Fine | Lubricant | 1.9 (+/−10%) | 1.9 (+/−10%) | 1.9 (+/−10%) | 3.1 (+/−10%) |
| Triethyl citrate NF | Plasticizer | 0.8 (+/−10%) | 0.8 (+/−10%) | 0.8 (+/−10%) | 1.25 (+/−10%) |
| Purified Water | Processing Agent | | | | |

Example 15a

Rasagiline Base 0.5 mg Enteric Coated Optional Formulation—with Citric Acid, Color Coated This example describes a 0.5 mg rasagiline base formulation containing citric acid with an extra color coating.

| Component | Function | Per Tablet (mg) |
|---|---|---|
| Core tablets | | |
| Rasagiline base | Drug Substance | 0.5 |
| Citric acid | Antioxidant | 1.6 |
| Mannitol | Filler | 80.3 |
| Aerosil | Flowing Agent | 0.6 |
| Starch, Pregelatinized (Starch STA-RX 1500) | Disintegrant | 20.0 |
| Starch NF | Binder | 10.0 |
| Talc | Lubricant | 2.0 |
| Stearic Acid | Lubricant | 2.0 |
| Total Core Tablet weight | | 117.0 |
| Subcoating | | |
| Pharmacoat 606 (Hypromellose USP) Granules | Coating Agent | 4.8 |
| Purified Water | Processing Agent | |
| Coating Suspension | | |
| Eudragit L-30D-55 | Coating Agent | 6.25* |
| Talc USP Extra Fine | Lubricant | 3.1 |
| Triethyl citrate NF | Plasticizer | 1.25 |
| Purified Water | Processing Agent | |
| Top coat | | |
| OPADRY II OY-GM-28900 WHITE (catnum. 415850005) OR OPADRY II Y-30-18037 WHITE (catnum. 415880719) OR/AND Opadry fx 63f97546 silver | Coating Agent | 1-5 |
| Purified Water | Processing Agent | |

*Dry substance remaining on the core.

Example 15b

Rasagiline Base 1 mg Enteric Coated Optional Formulation—with Citric Acid, Color Coated This example describes a, 1 mg rasagiline base formulation containing citric acid with an extra color coating.

| Component | Function | Per Tablet (mg) |
|---|---|---|
| Core tablets | | |
| Rasagiline base | Drug Substance | 1.0 |
| Citric acid | Antioxidant | 1.6 |
| Mannitol | Filler | 79.8 |
| Aerosil | Flowing Agent | 0.6 |
| Starch, Pregelatinized (Starch STA-RX 1500) | Disintegrant | 20.0 |
| Starch NF | Binder | 10.0 |
| Talc | Lubricant | 2.0 |
| Stearic Acid | Lubricant | 2.0 |
| Total Core Tablet weight | | 117.0 |
| Subcoating | | |
| Pharmacoat 606 (Hypromellose USP) Granules | Coating Agent | 4.8 |
| Purified Water | Processing Agent | |
| Coating Suspension | | |
| Eudragit L-30D-55 | Coating Agent | 6.25* |
| Talc USP Extra Fine | Lubricant | 3.1 |
| Triethyl citrate NF | Plasticizer | 1.25 |
| Purified Water | Processing Agent | |
| Top coat | | |
| Opadry ® II 31F20721 Blue OR Opadry ® II 34G24627 Pink OR/AND Opadry fx 63f97546 silver | Coating Agent | 1-5 |
| Purified Water | Processing Agent | |

*Dry substance remaining on the core.

Example 16a

Rasagiline Base 0.5 mg Enteric Coated Optional Formulation—with Malic Acid, Color Coated This example describes a 0.5 mg rasagiline base formulations containing malic acid with an extra color coating.

| Component | Function | Per Tablet (mg) |
|---|---|---|
| Core tablets | | |
| Rasagiline base | Drug Substance | 0.5 |
| Malic acid | Antioxidant | 1.6 |
| Mannitol | Filler | 80.3 |
| Aerosil | Flowing Agent | 0.6 |
| Starch, Pregelatinized (Starch STA-RX 1500) | Disintegrant | 20.0 |
| Starch NF | Binder | 10.0 |
| Talc | Lubricant | 2.0 |
| Stearic Acid | Lubricant | 2.0 |
| Total Core Tablet weight | | 117.0 |
| Subcoating | | |
| Pharmacoat 606 (Hypromellose USP) Granules | Coating Agent | 4.8 |
| Purified Water | Processing Agent | |
| Coating Suspension | | |
| Eudragit L-30D-55 | Coating Agent | 6.25* |
| Talc USP Extra Fine | Lubricant | 3.1 |
| Triethyl citrate NF | Plasticizer | 1.25 |

Example 16b

Rasagiline Base 1 mg Enteric Coated Optional Formulation—with Malic Acid, Color Coated This example describes a 1 mg rasagiline base formulations containing malic acid with an extra color coating.

| Component | Function | Per Tablet (mg) |
|---|---|---|
| Core tablets | | |
| Rasagiline base | Drug Substance | 1.0 |
| Malic acid | Antioxidant | 1.6 |
| Mannitol | Filler | 79.8 |
| Aerosil | Flowing Agent | 0.6 |
| Starch, Pregelatinized (Starch STA-RX 1500) | Disintegrant | 20.0 |
| Starch NF | Binder | 10.0 |
| Talc | Lubricant | 2.0 |
| Stearic Acid | Lubricant | 2.0 |
| Total Core Tablet Weight | | 117.0 |
| Subcoating | | |
| Pharmacoat 606 (Hypromellose USP) Granules | Coating Agent | 4.8 |
| Purified Water | Processing Agent | |
| Coating Suspension | | |
| Eudragit L-30D-55 | Coating Agent | 6.25* |
| Talc USP Extra Fine | Lubricant | 3.1 |
| Triethyl citrate NF | Plasticizer | 1.25 |
| Purified Water | Processing Agent | |
| Top coat | | |
| Opadry ® II 31F20721 Blue OR Opadry ® II 34G24627 Pink OR/AND Opadry fx 63f97546 silver | Coating Agent | 1-5 |
| Purified Water | Processing Agent | |

*Dry substance remaining on the core.

Example 17

Extraction of Rasagiline Base from Tablets

The aim of the study was to evaluate the amount of free Rasagiline base in 1 mg tablets of "Citric" formulation.

Rasagiline is assumed to present in the formulation in salt form or as free base.

Rasagiline base is a non-polar compound very soluble in non-polar organic solvents such as hexane toluene and ethylacetate. Therefore, free Rasagiline base could be extracted from the solid formulation by these solvents.

Rasagiline salts are not soluble in non-polar solvents and probability of the extraction of rasagiline citrate with hexane, toluene, 1-octanol or ethylacetate is very low.

Core tablets of Rasagiline base prepared using steps described in example 9 were tested. Each tablet contained 1 mg of Rasagiline base. Placebo tablets were used as references.

17 core tablets, 1 mg of Rasagiline base each were crushed and ground in mortar to homogeneous fine powder.

Each powder was mixed with 20 ml of organic solvent and stirred with magnetic stirrer for 1 hour at room temperature in closed glass vessel. Then the mixture was settled without stirring, the clear liquid was decanted and a sample of the resulting extract was filtered trough 0.2µ filter.

The filtered samples of the extracts were subjected to HPLC analysis for quantity of dissolved Rasagiline. Samples of the placebo extracts were used as control.

Maximal possible calculated concentration of Rasagiline base in the extracts is 0.85 mg/ml (17 mg in 20 ml solvent).

The results are summarized in Table 5 below.

TABLE 5

Extractions of Rasagiline base from core tablets with organic solvents

| Experiment No. | No. of tablets | Weight of tablets, g | Solvent | Achieved concentration of Rasagiline in extract, mg/ml |
|---|---|---|---|---|
| 1 | 17 | 2.02 | Toluene | 0.01 |
| 2 | 17 | 2.02 | n-Hexane | 0.01 |
| 3 | 17 | 2.02 | DCM | 0.01 |
| 4 | 17 | 2.03 | 1-Octanol | 0.01 |
| 5 | 17 | 2.02 | Ethyl acetate | 0.02 |

Summary of Results

The experimental results in Table 5 show that the core tablets of "Citric" formulation of Rasagiline base may contain 1 to 2 percent of the free rasagiline base extractable with non polar solvents.

Amount of the extractable base does not depend on the solvent type for non polar solvent as n-hexane, toluene, 1-octanol and dichloromethane.

At the same time more polar solvent as ethylacetate extracted more Rasagiline from the core tablets.

Example 18

Clinical Study Based on Tablets According to Examples 3a and 3b

This study evaluates the bioavailability of two different rasagiline base 1 mg enteric coated tablet formulations prepared according to each of Examples 3a (Formulation I) and 3b (Formulation III) verses the marketed rasagiline drug product (Azilect 1 mg) following a single dose administration, and to assess the effect of food on each one of the test formulations.

This study also evaluates the safety and tolerability of each treatment.

1. Study Design

This study is a flexible two-part protocol, each part testing the bioavailability of a different rasagiline base 1 mg enteric coated formulation (Formulation I or Formulation III) against the reference product (Azilect® 1 mg).

Each part is an open-label, three-period, three-sequence, comparative crossover study in 15 healthy males and females (5 per sequence).

Treatment A: One Rasagiline Base 1 mg Enteric Coated Tablets (test Formulation I or test Formulation III) in the fasted state.

Treatment B: One Azilect® tablet (reference 1 mg rasagiline as rasagiline mesylate) in the fasted state.

Treatment C: One Rasagiline Base 1 mg Enteric Coated Tablets (test Formulation I or test Formulation III) following a standardized high-fat, high-calorie meal.

The 3 treatments are administered across 3 study periods each of which is separated by a 14-day washout interval. They are administered according to one of three sequences to which subjects are randomly assigned: A-B-C, B-C-A, or C-A-B.

In each period, subjects are confined for two overnight stays [at least 10.5 hours prior to and until at dose administration]. Subjects return for an ambulatory blood sample collection (36 hours) on Day 2.

In Part 1, Subjects 1-15 receive test Formulation I or reference, while in Part 2, Subjects 16-30 receive test Formulation III or reference. The decision to proceed with each study part is based on the availability of the test Formulation.

AEs, vital signs, physical examination, and clinical laboratory tests are assessed for safety and blood samples are taken at regular pre-defined time points throughout the study for the measurement of rasagiline and aminoindan concentrations in plasma.

2. Subject Selection

Thirty (30) healthy adult (~50%/50% male and female) subjects are selected from non-institutionalized subjects consisting of members of the community at large.

3. Pharmacokinetic (PK) Sampling and Analysis

A total of 80 samples (about 400 mL) are drawn from each subject for PK purposes. Pharmacokinetic sampling occurs at the following timepoints:

a) Treatment A (test, fasted):
Day 1 within 90 minutes prior to dosing (0 hour) and after dose administration at 0.5, 0.75, 1, 1.33, 1.67, 2, 2.33, 2.67, 3, 3.33, 3.67, 4, 4.5, 5, 6, 7, 8, 9, 12, 24 and 36 hours (22 samples).

b) Treatment B (reference, fasted):
Day 1 within 90 minutes prior to dosing (0 hour) and after dose administration at 0.25, 0.5, 0.75, 1, 1.25, 1.5, 2, 3, 4, 5, 6, 7, 8, 12, 24 and 36 hours (17 samples).

c) Treatment C (test, fed):
Day 1 within 90 minutes prior to dosing (0 hour) and after dose administration at 1, 1.5, 2, 2.5, 3, 3.33, 3.67, 4, 4.33, 4.67, 5, 5.33, 5.67, 6, 6.33, 6.67, 7, 7.33, 7.67, 8, 8.5, 9, 10, 11, 12, 13, 14, 15, 16, 18, 19, 20, 21, 22, 23, 24, 25, 26 and 36 hours (41 samples).

Blood are drawn either by direct venipuncture or through an indwelling intravenous cannula. Whenever the latter is performed, the cannula is flushed with 1.5 mL normal saline after each sampling. In addition, to avoid sample dilution, 1 mL blood is discarded before the next sample (as long as the cannula is in place). Therefore, up to 5 mL blood is collected at each time point. The total blood volume taken per subject for pharmacokinetic sampling is approximately 400 ml over a 4-week period.

Samples are collected into appropriate volume K2-EDTA vacutainers. The labels for all biological sample collection and storage containers contain, at a minimum, Protocol Number, Sub-study number, Subject Number; Dosing Period; Dosing Day; PK time point. Immediately following sample collection, samples are mixed by inverting the collection tube at least 2-3 times. Samples are cooled by an ice bath or cooling device until processed. Blood processing occur within 2 hours of collection: the sample is centrifuged at approximately 2000 g and 4° C. (±3° C.) for about 10 minutes, the plasma transferred into appropriately labeled duplicate polypropylene tubes, and stored at approximately −20° C. until transfer or shipment to the bioanalytical laboratory. At least 0.7 mL of plasma is transferred into the first polypropylene tube and the remaining plasma is transferred to the second polypropylene tube. The time at which samples are placed at −20° C. are recorded in the study documentation.

Actual sampling time is recorded directly in the source data or CRF. Sample processing procedures are documented in the PK logbook.

The rasagiline and aminoindan plasma concentrations are measured using a validated LC/MS/MS bioanalytical method and according to the Bioanalytical Laboratory's Standard Operating Procedures and FDA Guidelines.

Analysis of the PK data of each sub-study is performed separately, according to audited bioanalytical data availability. The individual plasma concentrations of rasagiline and aminoindan are listed, displayed graphically as appropriate and summarized using descriptive statistics for each of the treatments.

Pharmacokinetic analysis are performed with rasagiline and aminoindan concentration profiles using appropriate non-compartmental methods.

The following parameters are calculated: $C_{max}$, $t_{max}$, $t_{lag}$, $AUC_t$, $AUC_\infty$, $t_{1/2}$, CL/F, V/F, % $AUC_{ext}$, regression coefficient of the terminal slope. Additional PK parameters will be calculated if deemed necessary. All the PK parameters are listed and summarized using descriptive statistics.

Statistical analysis is performed using SAS for each sub-study based on the reception of the data. For each sub-study, bioequivalence between the test and reference formulations in the fasted state and the food effect on the test formulation are evaluated only for rasagiline, according to 90% confidence intervals (CIs) of ratios of geometric means for $C_{max}$, $AUC_t$, and AUCoo. The ratios and CI are calculated using ANCOVA on the log-transformed data (MIXED procedure, SAS). The conclusion regarding bioequivalence are based on the back-transformed point estimate and CI. $T_{max}$ are analyzed using nonparametric analysis (Wilcoxon Signed Rank Test).

4. Results

Bioequivalence Tests

The testing results show that the delayed release formulations tested (Formulation I and Formulation III) meets the criteria for bioequivalence to the known immediate release formulation. Each of the $C_{max}$ and $AUC_t$ achieve a range of 80-140% within a 90% confidence interval between the formulation tested and the reference immediate release formulation.

MAO Assay:

The testing results show MAO-B activity for formulation prepared according to each of the Examples 3a and 3b are comparable to the reference immediate release formulation.

The standard method is used for the enzymatic determination of MAO: "Determination of monoamine oxidase (MAO) by an extraction method using radiolabelled substrate in various tissues".

Briefly, fifty (50) µl of homogenate are added to 100 µl 0.1 M phosphate buffer (pH-7.4). After preincubation of 20 minutes at 37° C., 50 µl of $^{14}$C-phenylethylamine hydrochloride (10 µM final concentration) are added and incubation continued for next 20 minutes. The reaction is then stopped by addition of citric acid 2 M.

Radioactive metabolites are extracted into toluene/ethyl acetate (1:1 v/v.), a solution of 2,5-diphenyloxazole is added to a final concentration of 0.4% and the metabolite content is estimated by liquid scintillation counting.

Activity of rat brain homogenate serves as standard (positive control) to the assay.

Protein determination is performed by the Lowrey method.

Safety and Tolerability

The testing results show that safety and tolerability for each treatment are acceptable.

Example 19

Additional Studies Based on Tablets According to Examples 3c. 3d, 6a-6d and 9-16

Additional studies are conducted evaluating the bioavailability of two different rasagiline base 1 mg enteric coated tablet formulations prepared according to each of Examples 3c, 3d, 6a-6d and 9-16 verses the marketed rasagiline drug product (Azilect 1 mg) following a single dose administration, and the effect of food on each one of the test formulations.

The results show that all of these formulations tested have acceptable bioavailability characteristics and MAO-B activity.

What is claimed is:

1. A stable oral dosage form comprising a core having mono-rasagiline citrate and at least one pharmaceutically acceptable excipient; and an acid resistant pharmaceutically acceptable coating.

2. The dosage form of claim 1, wherein the dosage form when ingested by a human subject provides an AUC value of rasagiline of 80-130% of that of the corresponding amount of rasagiline ingested as an immediate release formulation.

3. The dosage form of claim 2, which upon administration to a human subject provides an AUC value of rasagiline of 80-125% of that of the corresponding amount of rasagiline ingested as an immediate released formulation.

4. The dosage form of claim 1, wherein the dosage form when ingested by a human subject provides a $C_{max}$ of rasagiline 80-145% of that of the corresponding amount of rasagiline ingested as an immediate release formulation.

5. The dosage form of claim 4, which when ingested by a human subject provides a $C_{max}$ of rasagiline of 80-125% of that of the corresponding dosage of rasagiline ingested as an immediate release formulation.

6. The dosage form of claim 1, wherein the core further comprises at least one anti-oxidant.

7. The dosage form of claim 6, wherein the ant oxidant is citric acid.

8. The dosage form of claim 1, wherein the core is in the form of a tablet.

9. The dosage form of claim 1, wherein the core further comprises at least one disintegrant.

10. The dosage form of claim 9, wherein the core comprises between 0.5% and 20% by weight of disintegrant.

11. The dosage form of claim 9, wherein the disintegrant is pre-gelatinized starch.

12. The dosage form of claim 1, wherein the acid resistant coating layer comprises methacrylic acid-ethyl acrylate copolymer (1:1) and a plasticizer.

13. The dosage form of claim 12, wherein in the acid resistant coating layer the ratio of methacrylic acid-ethyl acrylate copolymer (1:1) to plasticizer is between 10 to 1 and 2 to 1.

14. The dosage form of claim 13, wherein in the coating the ratio of methacrylic acid-ethyl acrylate copolymer (1:1) to plasticizer is 5 to 1.

15. The dosage form of claim 12, wherein the plasticizer is triethyl citrate.

16. The dosage form of claim 12, wherein the acid resistant coating layer further comprises talc.

17. The dosage form of claim 1, wherein the acid resistant coating is between 3% and 12% by weight of the dosage form.

18. The dosage form of claim 17, wherein the acid resistant coating is 8% by weight of the dosage form.

19. The dosage form of claim 1, wherein the acid resistant coating comprises two coating layers.

20. The dosage form of claim 19, wherein the inner one of the two coating layers comprises hypromellose.

21. The dosage form of claim 1, which is less than 150 mg by weight.

22. The dosage form of claim 1, wherein the content of rasagiline citrate is 0.74 mg to 3.63 mg.

23. The dosage form of claim 1, wherein the content of rasagiline is 0.5 mg.

24. The dosage form of claim 1, wherein the content of rasagiline is 1.0 mg.

25. The dosage form of claim 1, which in addition to the mono-rasagiline citrate comprises mannitol, colloidal silicon dioxide, starch NF, pregelatinized starch, stearic acid, talc, hypromellose, methacrylic acid ethyl acrylate copolymer, talc extra fine, and triethyl citrate.

26. The dosage form of claim 25, comprising 79.84 mg of mannitol, 0.6 mg of colloidal silicon dioxide, 10.0 mg of starch NF, 20.0 mg of pregelatinized starch, 2.0 mg of stearic acid, 2.0 mg of talc, 4.8 mg of hypromellose, 6.25 mg of methacrylic acid-ethyl acrylate copolymer, 1.25 mg of triethyl citrate, and 3.1 mg of talc extra fine.

27. The dosage form of claim 25, comprising 67.8 mg of mannitol, 0.6 mg of aerosil, 10.0 mg of starch NF, 20.0 mg of pregelatinized starch, 2.0 mg of stearic acid, 2.0 mg of talc, 4.8 mg of hypromellose, 4.0 mg of methacrylic acid ethyl acrylate copolymer, 0.8 mg of triethyl citrate, and 1.9 mg of talc extra fine.

28. The dosage form of claim 25, comprising 80.34 mg of mannitol, 0.6 mg of aerosil, 10.0 mg of starch NF, 20.0 mg of pregelatinized starch, 2.0 mg of stearic acid, 2.0 mg of talc, 4.8 mg of hypromellose, 6.25 mg of methacrylic acid ethyl acrylate copolymer, 1.25 mg of triethyl citrate, and 3.1 mg of talc extra fine.

29. The dosage form of claim 25, comprising 68.3 mg of mannitol, 0.6 mg of aerosil, 10.0 mg of starch NF, 20.0 mg of pregelatinized starch, 2.0 mg of stearic acid, 2.0 mg of talc, 4.8 mg of hypromellose, 4.0 mg of methacrylic acid ethyl acrylate copolymer, 0.8 mg of triethyl citrate, and 1.9 mg of talc extra fine.

30. The dosage form of claim 1, which releases between 80 and 100% of rasagiline when placed in a basket apparatus in 500 mL of buffered aqueous media at a pH of 6.8 at 37° C. at 75 revolutions per minute for 20 minutes.

31. The dosage form of claim 1, further comprising rasagline base.

32. The dosage form of claim 1, wherein up to 2% of the total amount of rasagiline in the dosage form is present as rasagiline free base.

33. The dosage form of claim 1, further comprising non-polar impurities.

34. The dosage form of claim 33, wherein the non-polar impurities comprises N-(2-Chloroallyl)-1(R)-aminoindan, and the amount of N-(2-Chloroallyl)-1(R)-aminoindan content in the dosage form is less than 20 ppm relative to the amount of rasagiline.

35. The dosage form of claim 34, wherein the amount of N-(2-Chloroallyl)-1(R)-aminoindan content in the dosage form is below quantitation limit.

36. The dosage form of claim 1, which when ingested by a human subject achieves MAO-B inhibition substantially the same as that of the corresponding dosage of rasagiline ingested as an immediate release formulation.

37. A method of treating a patient suffering from Parkinson's disease comprising administering to the patient the dosage form of claim 1.

38. The method of claim 37, wherein the patient suffers from delayed gastric emptying.

39. The dosage form of claim wherein the content of rasagiline in the core is 0.5 mg and the core comprises 45.5 mg of mannitol, 0.4 mg of aerosil, 5.0 mg of starch NF, 20.0 mg of pregelatinized starch, 1.5 mg of stearic acid, 1.5 mg of talc, and the acid resistant coating of the dosage form comprises two coating layers, of which the inner of the two coating layers comprises 3.5 mg of hypromellose and the outer of the two coating layers comprises 4.0 mg of methacrylic acid ethyl acrylate copolymer, 0.8 mg of triethyl citrate, and 1.9 mg of talc extra fine.

40. The dosage form of claim 25, wherein the content of rasagiline in the core is 1.0 mg and the core comprises 45.0 mg of mannitol, 0.4 mg of aerosil, 5.0 mg of starch NF, 20.0 mg of pregelatinized starch, 1.5 mg of stearic acid, 1.5 mg of talc, and the acid resistant coating of the dosage form comprises two coating layers, of which the inner of the two coating layers comprises 3.5 mg of hypromellose and the outer of the two coating layers comprises 4.0 mg of methacrylic acid ethyl acrylate copolymer, 0.8 mg of triethyl citrate, and 1.9 mg of talc extra fine.

41. The dosage form of claim 40, further comprising non-polar impurities which comprises N-(2-Chloroallyl)-1(R)-aminoindan and the amount of N-(2-Chloroallyl)-1(R)-aminoindan in the dosage form is less than 4 ppm relative to the amount of rasagiline.

\* \* \* \* \*